(12) United States Patent
Aizenberg et al.

(10) Patent No.: US 11,155,715 B2
(45) Date of Patent: Oct. 26, 2021

(54) STRUCTURALLY COLORED MATERIALS WITH SPECTRALLY SELECTIVE ABSORBING COMPONENTS AND METHODS FOR MAKING THE SAME

(71) Applicant: President and Fellows of Harvard College, Cambridge, MA (US)

(72) Inventors: Joanna Aizenberg, Boston, MA (US); Nicolas Vogel, Erlangen (DE); Ian Burgess, Toronto (CA); Mathias Kolle, Somerville, MA (US); Tanya Shirman, Arlington, MA (US); Stefanie Utech, Erlangen (DE); Katherine Phillips, Cambridge, MA (US); David A. Weitz, Bolton, MA (US); Natalie Koay, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 790 days.

(21) Appl. No.: 14/907,197

(22) PCT Filed: Jul. 13, 2014

(86) PCT No.: PCT/US2014/049288
§ 371 (c)(1),
(2) Date: Jan. 22, 2016

(87) PCT Pub. No.: WO2015/017722
PCT Pub. Date: Feb. 5, 2015

(65) Prior Publication Data
US 2016/0168386 A1   Jun. 16, 2016

Related U.S. Application Data
(60) Provisional application No. 61/860,694, filed on Jul. 31, 2013.

(51) Int. Cl.
*C09C 1/00* (2006.01)
*A61K 8/19* (2006.01)
(Continued)

(52) U.S. Cl.
CPC .......... *C09C 1/0081* (2013.01); *A61K 8/0283* (2013.01); *A61K 8/19* (2013.01);
(Continued)

(58) Field of Classification Search
CPC .......... A61K 2800/412; A61K 2800/43; A61K 2800/5922; A61K 8/0283; A61K 8/19;
(Continued)

(56) References Cited

U.S. PATENT DOCUMENTS

| 2005/0191774 | A1 | 9/2005 | Li et al. | |
| 2010/0239620 | A1* | 9/2010 | Butler | C09D 5/028 424/401 |
| 2014/0334005 | A1* | 11/2014 | Omenetto | B29D 11/0074 359/577 |

FOREIGN PATENT DOCUMENTS

| EP | 1736137 A1 | 12/2006 |
| JP | 2005-279633 A | 10/2005 |

(Continued)

OTHER PUBLICATIONS

International Search Report of International Application No. PCT/US2014/049288, International Filing Date Jul. 31, 2014, dated Sep. 15, 2015 (5 pages).
(Continued)

*Primary Examiner* — Shuangyi Abu Ali
(74) *Attorney, Agent, or Firm* — Wilmer Cutler Pickering Hale and Dorr LLP

(57) ABSTRACT

A structurally colored pigment is described that contains a plurality of photonic crystal particles dispersed in a medium, where each photonic crystal particles contains a plurality of
(Continued)

Formula for estimation of skin depth
skin depth (# of periods) ~ $\lambda_0/w$ spectrally selective absorbing components dispersed within the photonic crystal particle. In certain embodiments, each photonic crystal particle has a predetermined minimum number of repeat units of the photonic crystal structure. The structurally colored material provides improved reflectance, long-term stability, and control of the desired optical effects. The fabrication techniques described herein also provide high throughput and high yield allowing use in wide ranging applications from cosmetics, paints, signs, sensors, to packaging material.

22 Claims, 28 Drawing Sheets

(51) Int. Cl.
*A61K 8/81* (2006.01)
*A61K 8/29* (2006.01)
*C09D 17/00* (2006.01)
*A61K 8/25* (2006.01)
*C09C 3/06* (2006.01)
*A61Q 1/02* (2006.01)
*C09C 1/62* (2006.01)
*A61K 8/02* (2006.01)
*A61Q 1/06* (2006.01)

(52) U.S. Cl.
CPC .................. *A61K 8/25* (2013.01); *A61K 8/29* (2013.01); *A61K 8/8176* (2013.01); *A61Q 1/02* (2013.01); *A61Q 1/06* (2013.01); *C09C 1/62* (2013.01); *C09C 3/06* (2013.01); *C09D 17/006* (2013.01); *A61K 2800/412* (2013.01); *A61K 2800/43* (2013.01); *A61K 2800/5922* (2013.01); *C01P 2004/64* (2013.01)

(58) Field of Classification Search
CPC .......... A61K 8/25; A61K 8/29; A61K 8/8176; A61Q 1/02; A61Q 1/06; C01P 2004/64; C09C 1/0081; C09C 1/62; C09C 3/06; C09D 17/006

See application file for complete search history.

(56) References Cited

FOREIGN PATENT DOCUMENTS

| | | | |
|---|---|---|---|
| JP | 2008-239588 | A | 10/2008 |
| JP | 2009/092616 | A | 4/2009 |
| JP | 2010-024289 | A | 2/2010 |
| JP | 2010-527342 | A | 8/2010 |
| JP | 2010/532738 | A | 10/2010 |
| JP | 2011-528808 | A | 11/2011 |
| WO | WO-2008/141971 | A2 | 11/2008 |
| WO | WO-2011/048570 | A2 | 4/2011 |
| WO | WO-2011045746 | A2 | 4/2011 |
| WO | WO-2012/078351 | A2 | 6/2012 |
| WO | WO-2013130156 | A2 | 9/2013 |

OTHER PUBLICATIONS

Written Opinion of the International Searching Authority of International Application No. PCT/US2014/049288, International Filing Date Jul. 31, 2014, dated Sep. 15, 2015, (5 pages).

Aguirre et al., "Tunable Colors in Opals and Inverse Opal Photonic Crystals," Advanced Functional Materials, vol. 20, No. 6, pp. 2565-2578, Aug. 23, 2010.

European Search Report dated Jan. 16, 2017 in European Application No. 14832865.1, 14 pages.

* cited by examiner

STRUCTURALLY COLORED MATERIALS WITH SPECTRALLY SELECTIVE ABSORBING COMPONENTS AND METHODS FOR MAKING THE SAME

CROSS-REFERENCES TO RELATED APPLICATIONS

This patent application claims the benefit of the earlier filing date of International Patent Application No. PCT/US2014/049288, filed on Jul. 31, 2014, which claims the benefit of U.S. patent application Ser. No. 61/860,694, filed on Jul. 31, 2013, the contents of which are incorporated by reference herein in its entirety.

STATEMENT REGARDING FEDERALLY SPONSORED RESEARCH OR DEVELOPMENT

The present invention was partially made with United States government support under Grant No. FA9550-09-1-0669-DOD35CAP awarded by the Air Force Office of Scientific Research. The United States government may have certain rights in this invention.

COPYRIGHT NOTICE

This patent disclosure may contain material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The present application relates to color science. More particularly, the present application relates to providing structurally colored materials providing a desired set of properties that can be used in a wide range of applications.

BACKGROUND

The use of colored chemical pigments exhaustively abounds in everyday life and is the predominant method for achieving colors ranging the entire visible spectrum. However, such organic pigments have potential toxicity as well as bleaching tendencies over longer period of use.

Photonic crystals demonstrate strong, adjustable color originating from the geometry of the system (so-called, structural color) and are thus, a potential candidate for innovative new non-bleaching and environmentally benign pigments. However, as their color arises from interference effects, control of the observed color based on viewing angle remains problematic. Moreover, when photonic crystal particulates with finite sizes below a certain size limit are formed as coloring agents, the interference effects decay and multiple scattering becomes more prominent leading to white colored pigments.

Some recent efforts have produced inverse opal microparticles loaded with carbon nanopowder. However, due to the broadband absorption at visible wavelengths, those materials suffer from poor reflectance and dull colors.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1A:
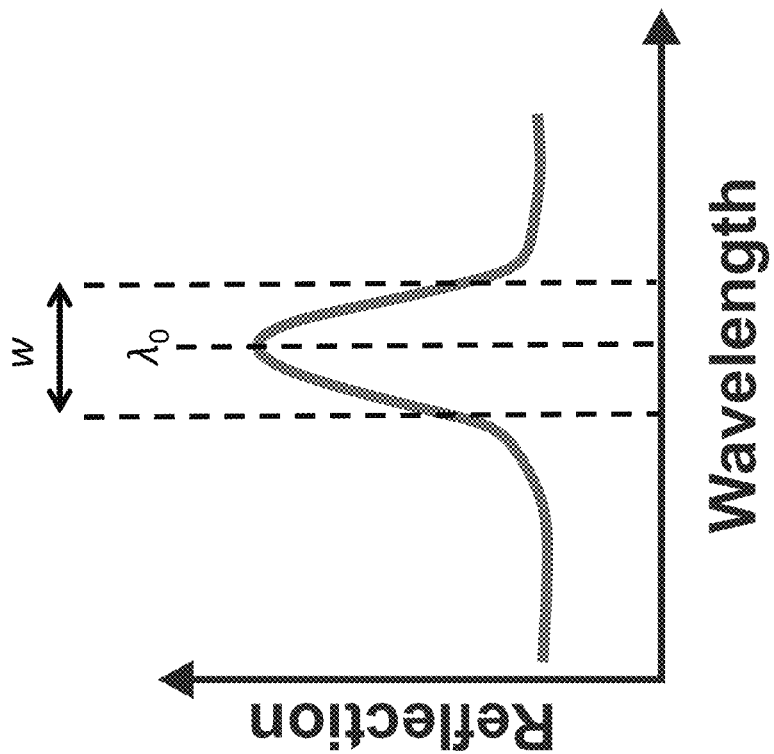
FIGS. 1A-1B demonstrate the minimum number of repeat units of the photonic crystal can be determined based on the reflected wavelength, full width at half maximum and refractive index contrast in accordance with certain embodiments.

In certain embodiments, structurally colored materials are provided by embedding spectrally selective absorbing components inside a photonic crystal particle.

In certain embodiments, precise adjustment of observed color can be obtained by varying porosity and periodicity, and the size of the photonic crystal particles as well as tailoring the optical properties using spectrally selective absorbing components. For instance, the spectrally selective absorbing components can suppress unwanted colors while the porosity, periodicity and the size of the photonic crystal particles can be tailored to produce resonant wavelengths of sufficiently strong intensity. In particular, the size of the photonic crystal particles can be tailored so that they are larger than a minimum number of repeat units to produce a sufficiently strong color.

In certain embodiments, when a constant color is desired regardless of the observation angle, a degree of disorder into the photonic crystal structure may be introduced, which can lead to a larger minimum number of repeat units. Alternatively, if sparkle effects or iridescence is desired, each photonic crystal particle may be produced with a high degree of order. For example, a photonic crystal particle having a high degree of order can lead to a different color depending on the angle of observation, which can provide the sparkle or iridescence effect.

In certain embodiments, when a constant color is desired regardless of the observation angle, smaller photonic crystal particles can be utilized. In contrast, if sparkle effects or iridescence is desired, larger photonic crystal particles can be utilized.

In certain embodiments, a plurality of photonic crystal particles containing spectrally selective absorbing components are provided together for use as a pigment. For example, the plurality of photonic crystal particles containing spectrally selective absorbing components can be utilized as pigments, such as a lipstick, paste, and the like.

In certain embodiments, the pigment can include a plurality of photonic crystal particles containing spectrally selective absorbing components dispersed in a suitable medium, such as water, organic solvents, oils, and the like. For example, photonic crystal particles described herein can be dispersed in a medium or be a part of the complex paint, and the like. In certain embodiments, the photonic crystal particles can be present in concentrations ranging from about 0.1 to 50 vol %. The pigment dispersed in a suitable medium can further include other components, such as surfactants, dispersants, shear thickening agents, shear thinning agents, spreading agents, adhesion promoters, polymers, film-forming agents, co-solvents to control viscosity or evaporation, thickeners, viscosity modifying agents, stabilisers, and the like.

In certain embodiments, the photonic crystal particles described herein can be functionalized for improved dispersion in a carrier material or dispersion medium. In certain embodiments, the photonic crystal particles described herein can be functionalized so that resistance to loss of structural color by lowered refractive index contrast due to the carrier material or dispersion medium can be achieved. For example, photonic crystal particles having a functionalized outer shell can be used inside oil for cosmetic effect, and the functionalized outer shell may help to reduce penetration of the oil inside the photonic crystal particles to stably maintain the bright structural color.

Even further benefits can include UV protection (when a UV-absorbing materials such as titania and the like, are used as part of the structure), photocatalysis, antimicrobial properties and anti-inflammatory properties (arising from, for example, antimicrobial function of silver nanoparticles and the like), controlled release of molecules (e.g., perfume, medicine, drugs, etc.), controlled absorption of molecules (e.g., oils having mattifying effect, etc.). In certain embodiments, benign, non-toxic materials such as minerals, which are also biodegradable, can be utilized.

In certain embodiments, spatially controlled surface functionalization can be introduced to tune the macroscale wetting properties, producing dynamic colors capable of reacting to changing environmental conditions.

Photonic Crystal Particles

In certain embodiments, photonic crystal particles having a resonant frequency near the desired color range can be utilized. As used herein, "photonic crystal" structures refer to structures that have at least some level of periodic variations in space of materials having a high dielectric constant and a low dielectric constant. As used herein, "photonic crystal" need not mean a structure having perfect crystalline order, but can tolerate some degree of defects. For example, "photonic crystal" can include structures that have some level of short-and long-range periodic variations in space of materials having a high dielectric constant and a low dielectric constant. Photonic crystal structures can affect the propagation of electromagnetic waves, such as visible light.

In certain embodiments, the periodic variations in space can occur in one-dimension, two-dimensions, or three-dimensions. In certain embodiments, periodically structured materials with a periodicity matching the wavelength of visible light can be utilized. Some exemplary photonic crystal structures include multilayer stacks, inverse opals, anodized alumina structures, woodpile structures, direct opals, highly ordered nano-wire forests, diffraction gratings, planar 2D photonic crystals, and the like.

In certain embodiments, the photonic crystals can be formed using one or more of ceramic materials such as silica, titania, zirconia, alumina, and the like and their mixtures; complex oxides; organic polymeric materials; inorganic polymeric materials such as silicone and the like; organic and inorganic mineral salts and crystals such as carbonates, sulfates, phosphates, and the like; mixed salts; other minerals such as quartz, sapphire and the like; metals and metal alloys; silicon, and the like and combinations thereof. In certain aspects, the high refractive index material can be formed using silica, tiania, zirconia, other ceramic materials and their mixtures, polymeric materials, and the like. Other exemplary materials include metal oxides, mixed metal oxides, doped metal oxides, polymers, inorganic salts, silicon, germanium, tin, silicon doped with group III or V elements, germanium doped with group III or V elements, tin doped with group III or V elements, silica, alumina, beryllia, noble metal oxides, platinum group metal oxides, titania, zirconia, hathia, molybdenum oxides, tungsten oxides, rhenium oxides, tantalum oxide, niobium oxide, chromium oxides, scandium, yttrium, lanthanum, ceria, and rare earth oxides, thorium and uranium oxide, inorganic sol-gel derived oxides, polymers, random copolymers, block copolymers, branched polymers, star polymers, dendritic polymers, supramolecular polymers and the like. In certain aspects, the low dielectric material can be formed using air, water, organic solvents, oil, vaporized liquids, emulsions, polymeric materials, gases or combinations thereof. In certain embodiments, even inorganic oxides, metals, polymeric materials, liquids can be utilized as long as there is a higher index material used along with it. Any combination of the high dielectric material and the low dielectric material described herein can be utilized. Generally, the technique is not limited to any particular material described herein; any materials combination can be utilized as long as there is a refractive index difference between the high dielectric material and a low dielectric material.

In certain embodiments, the photonic crystal can be formed to exhibit a predetermined wavelength of constructive interference, referred to herein as a "resonant wavelength." In certain embodiments, "resonant wavelength" refers to the peak wavelength among a range of wavelengths, but can also include a range of wavelengths near the peak wavelength, such as a peak with a full width at half maximum (FWHM) of about 100 nm, 40 nm, 40 nm, 20 nm or 10 nm. Depending on the desired color and the type of photonic crystal structure, the FWHM may be larger or smaller. In one aspect, the photonic crystal can be formed to have a resonant wavelength of about 650 nm to exhibit a red structural color. In another aspect, the photonic crystal can be formed to have a resonant wavelength of about 600 nm to exhibit an orange structural color. In another aspect, the photonic crystal can be formed to have a resonant wavelength of about 570 nm to exhibit a yellow structural color.

In another aspect, the photonic crystal can be formed to have a resonant wavelength of about 510 nm to exhibit a green structural color. In another aspect, the photonic crystal can be formed to have a resonant wavelength of about 475 nm to exhibit a blue structural color. In another aspect, the photonic crystal can be formed to have a resonant wavelength of about 445 nm to exhibit an indigo structural color. In another aspect, the photonic crystal can be formed to have a resonant wavelength of about 400 nm to exhibit a violet structural color. Generally, the photonic crystal can be formed to have a resonant wavelength that corresponds to any arbitrary color or hue.

For example, for the case of inverse opal structures formed by silica and air, the optical periodicity of the photonic crystal structure can be on the order of about 325 nm to exhibit a red structural color. As used herein, "optical periodicity" of a photonic crystal structure refers to a repeat unit distance between a high dielectric material and a low dielectric material in terms of optical path. As used herein "optical path" refers to the measure of distance that conserves the number of wavelengths light travels between two points. The optical path between two points inside a homogeneous material having constant refractive index is defined by the distance between two points multiplied by the refractive index of the material. In certain embodiments, the optical path of periodicity of the photonic crystal can be on the order of about 300 nm to exhibit an orange structural color. In certain embodiments, the optical path of periodicity of the photonic crystal can be on the order of about 285 nm to exhibit a yellow structural color. In certain embodiments, the optical path of periodicity of the photonic crystal can be on the order of about 255 nm to exhibit a green structural color. In certain embodiments, the optical path of periodicity of the photonic crystal can be on the order of about 238 nm to exhibit a blue structural color. In certain embodiments, the optical path of periodicity of the photonic crystal can be on the order of about 223 nm to exhibit an indigo structural color. In certain embodiments, the optical path of periodicity of the photonic crystal can be on the order of about 200 nm to exhibit a violet structural color. Generally, the optical path of periodicity of the photonic crystal can be designed to exhibit any arbitrary color or hue.

Figure 22:
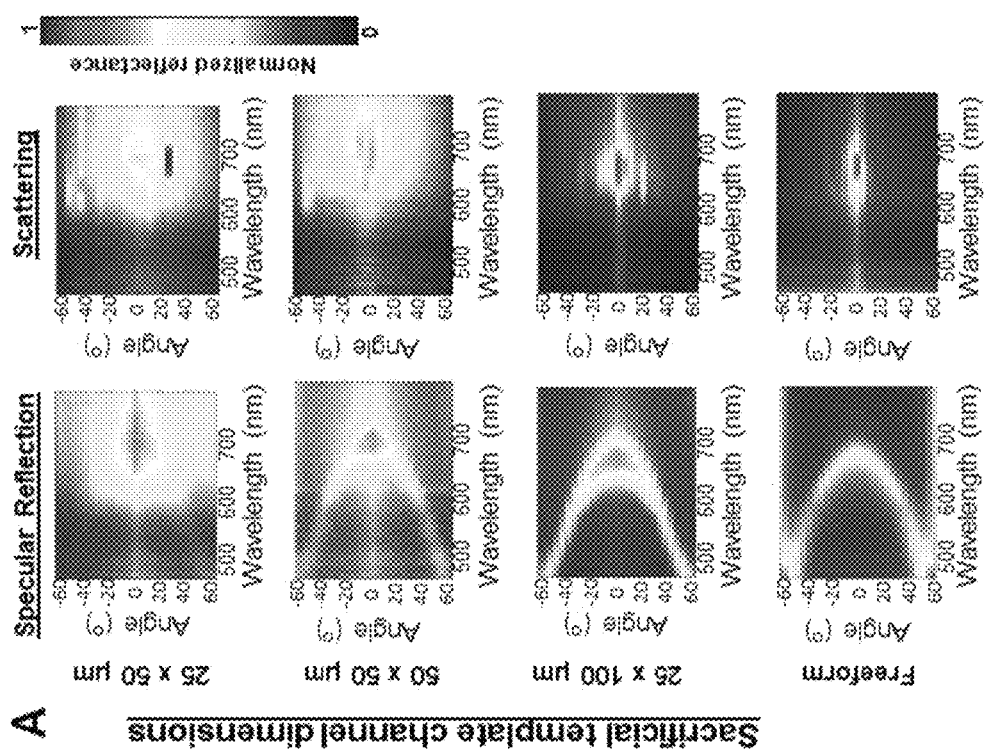
FIG. 22 demonstrates that larger photonic crystal particles provide a greater degree of sparkle, iridescence effects while smaller photonic crystal particles provide a more constant color at different observation angles.

In certain embodiments, the photonic crystal structure are fabricated in the form of particles. The photonic crystal particles require further consideration due to the smaller number of repeat units, as compared to photonic crystal structures fabricated in the form of films. For example, higher defects levels may be found in the form of particles due to the higher surface area where lattice structure can be distorted. Moreover, depending on the desired resonant wavelength and the particle size, a minimum particle size may be required to obtain sufficiently strong resonant effects of the photonic crystal structure. On the other hand, large photonic crystal particle can lead to sparkle effects and iridescence whereas small photonic crystal particles can provide a more uniform color. Depending on the size of the particles, more homogeneous coloration can be achieved using smaller particles or more vivid colors, including sparkle and iridescence, can be achieved using larger particles. For example, as shown in FIG. 22, photonic crystal particles having a size of 25×50 µm exhibit a more uniform color at different observation angles. With larger photonic crystal particle size, angular dependence of the observed color becomes more pronounced, where a film (labeled "freeform") shows the highest degree of color change at different observation angles.

Figure 1B:
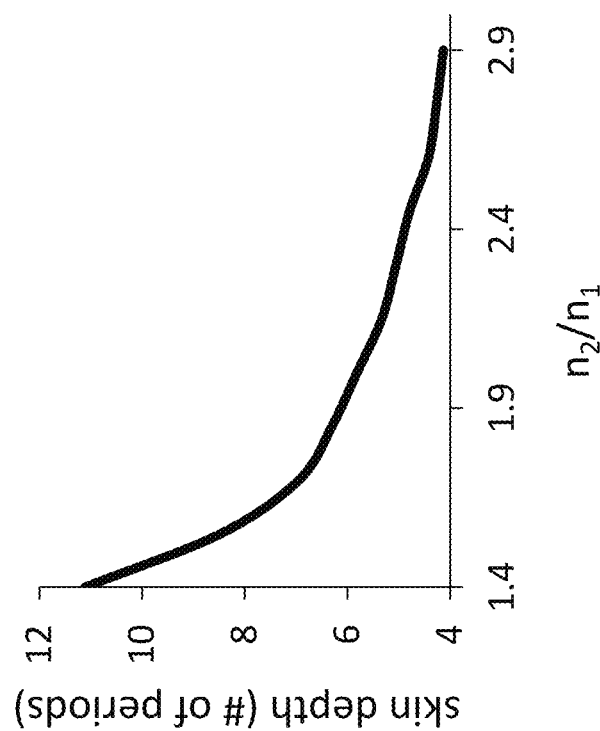

In certain embodiments, the photonic crystal particles having at least a predetermined minimum number of repeat units of the photonic crystal can provide particular benefits of improved color quality. As used herein, a "repeat unit" refers to a variation in space of materials having a high dielectric constant and a low dielectric constant. For example, as shown in FIGS. 1A-1B, for a given refractive index contrast of the photonic crystal ($n_2/n_1$), the minimum number of repeat units of the photonic crystal (skin depth) can be determined by calculating the reflection wavelength ($\lambda_o$) divided by the full-width at half maximum (w). The relationship between the skin depth as a function of the refractive index contrast of the photonic crystal ($n_2/n_1$) shown in FIG. 1A can be calculated for a particular photonic crystal structure (e.g., an inverse opal shown). The skin depth of a photonic crystal structure is related to its spectral selectivity. A photonic crystal structure that filters out the transmission of light at a reflection wavelength, $\lambda_o$, over a skin depth of N wavelengths will have a wavelength resolution that is limited to the order $\lambda_o/N$, giving its reflectance peak a full width at half maximum, $w \sim \lambda_o/2N$. Since photonic crystals have about two lattice periods of the photonic crystal structure per wavelength at the Bragg condition then the skin depth, $n_p$, expressed as the number of lattice periods of the photonic crystal structure, is related to w and $\lambda_0$ by $n_p \sim \lambda_o/w$. For a given refractive index contrast on the curve on FIG. 1A, the reflection wavelength ($\lambda_o$) and the full-width at half maximum (w) can be determined from simulations of the reflectance spectra for specific photonic crystal structures with a large number of lattice periods (much larger than $n_p$) using any number of methods such as transfer matrix calculations (see, e.g., A. Yariv, P. Yell, Photonics: Optical Electronics in Modern Communications, Oxford University Press, 2007, the relevant contents of which are incorporated herein by reference) or finite difference modeling (see, e.g., J. Joannopoulos, S. G. Johnson, J. Winn, R. Meade, Photonic Crystals: Molding the Flow of Light, Princeton University Press, 2008, the relevant contents of which are incorporated herein by reference). As shown, with higher refractive index contrast, a smaller number of repeat units can be utilized. For example, utilizing a refractive index contrast of about 2.9, about 4 repeat units can be utilized. In contrast, utilizing a refractive index contrast of about 1.4, about 12 repeat units can be utilized. However, additional repeat units, in addition to the predetermined minimum number of repeat units, can be utilized. In certain embodiments, the photonic crystal particles have a dimension that has at least 4, 6, 8, 10, 12, 13, 14, 15, 16, 17, 18, 19, 20, 25, 30, 50 repeat units of the photonic crystal structure. In certain embodiments, the photonic crystal particles have a dimension that is between 12-50 repeat units of the photonic crystal structure.

In certain embodiments, the photonic crystal particles can have any desired shape. For example, the photonic crystal particles can be isotropically shaped, such as a spherical ball, a cube, and the like. In other instances, the photonic crystal particles can be anisotropically shaped, such as a brick, elongated cylinder, ellipsoids, square prism, rectangular prism, various other prisms and pyramids, and the like. In yet other instances, the photonic crystal particulates can be other shapes, such as icosahedron, tetrahedral, pyramidal, rhombohedral, or any randomized structures.

Spectrally Selective Absorbing Components

In certain embodiments, the photonic crystal particles may contain spectrally selective absorbing components. In certain embodiments, the spectrally selective absorbing components can be present in concentrations ranging from about 0.1-10% by solid volume, such as from 0.1%-2.5% by solid volume. Greater amounts of the spectrally selective absorbing components can lead to greater suppression of the particular wavelengths outside of the resonant wavelengths of the photonic crystal particles. As used herein, spectrally selective absorbing components include components that selectively absorb some wavelengths without substantially absorbing the electromagnetic radiation near the resonant wavelengths of the photonic crystal.

Figures 2A, 2B, 2C:
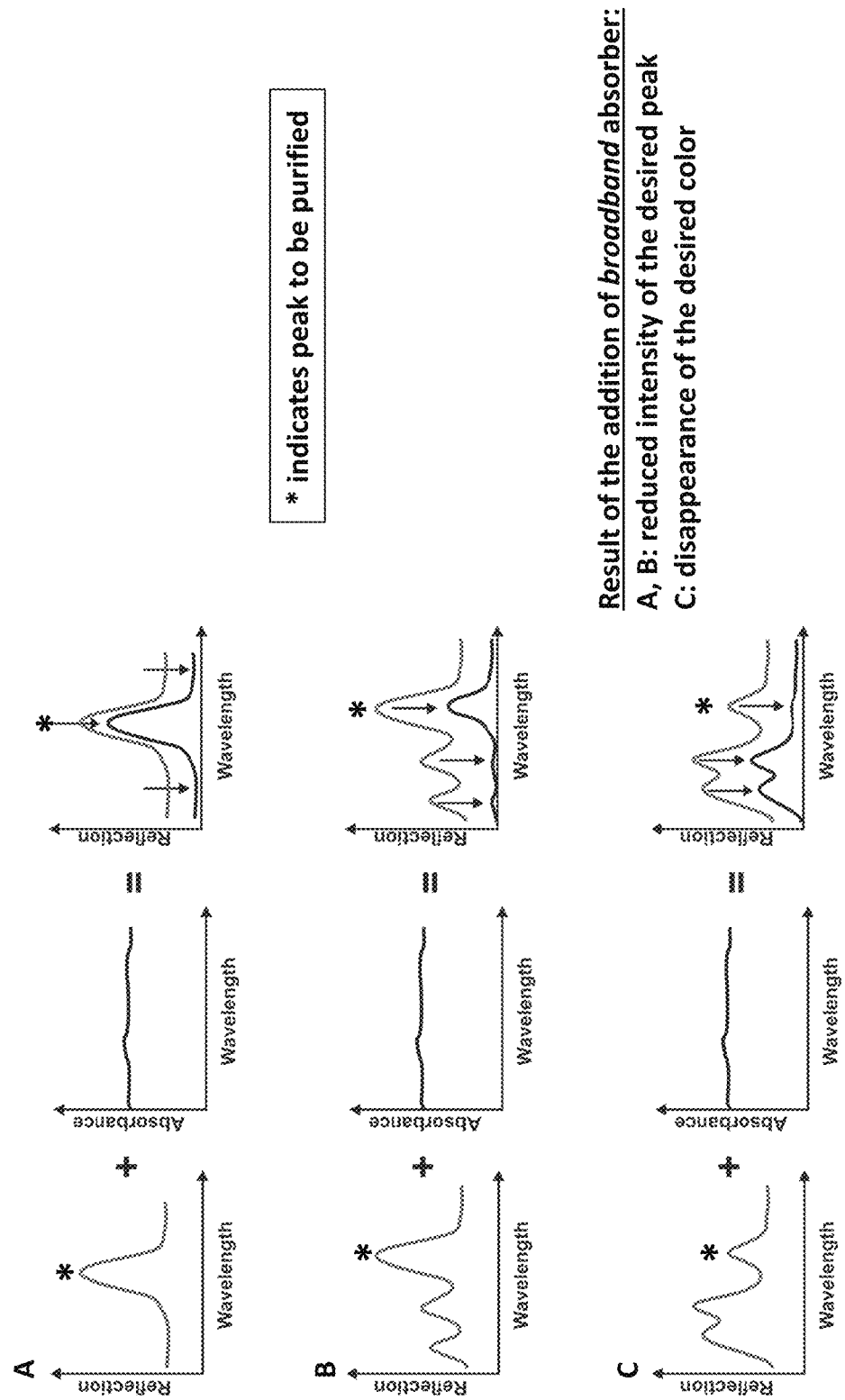
FIGS. 2A-2C provide a schematic illustration of photonic crystal particles mixed with broadband absorbers.

FIGS. 2A-2C show a photonic crystal that have been mixed with a broadband absorber in accordance with the conventional art. As shown, the * indicates the resonant wavelength of the photonic crystal. In some instances, as shown in FIGS. 2B and 2C, multiple resonant peaks may exist, where a particular desired wavelength for reflection is indicated with a *. As used herein, In each of these instances, when a broadband absorber, such as carbon nanoparticles, are utilized, suppression of all reflection intensity, including the intensity of the desired peak, is observed. In some cases, such as in FIG. 2C, when the desired color wavelength has a peak intensity that is lower than the other resonant wavelengths, disappearance of the desired color can even occur. For example, FIG. 2A shows a resonant peak.

Figures 2D, 2E, 2F:
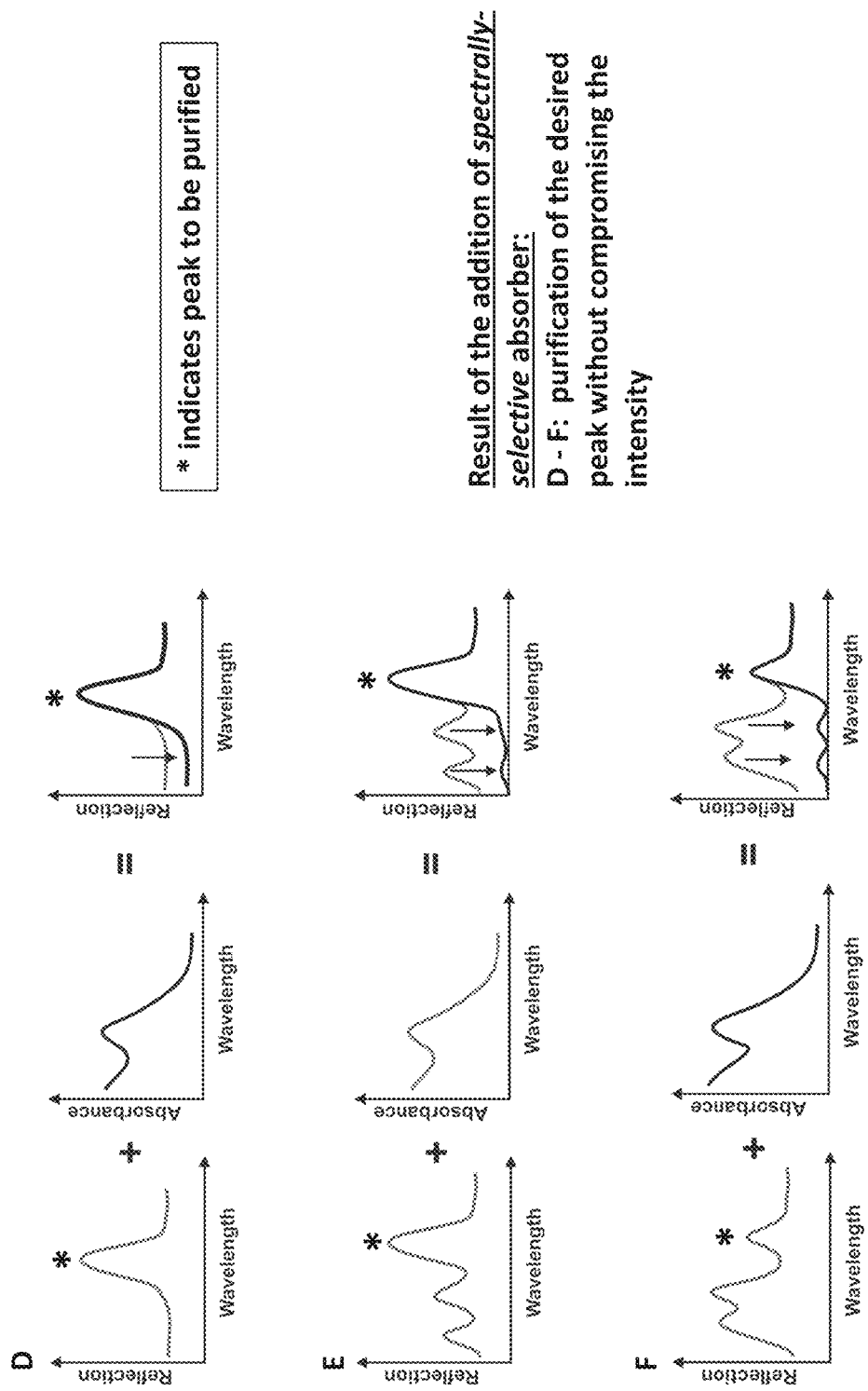
FIGS. 2D-2F provide a schematic illustration of photonic crystal particles mixed with spectrally selective absorbing components in accordance with certain embodiments.

In contrast, as shown in FIGS. 2D-2F, use of a photonic crystal with a spectrally selective absorber in accordance with certain embodiments lead to increasing the desired color while suppressing all the undesired colors. Unlike the conventional systems, use of the spectrally selective absorber leads to suppression of all the undesired colors such that even undesired colors of greater reflected intensity can be suppressed.

Any desired resonant wavelengths' reflection can be promoted while the undesired color wavelengths can be suppressed. For example, if the desired resonant wavelength was about 650 nm to produce a red structural color, the spectrally selective absorbing components can absorb one or more other visible wavelengths without substantially absorbing wavelengths of about 650 nm. As another example, if the desired resonant wavelength was about 600 nm to produce an orange structural color, the spectrally selective absorbing components can absorb one or more other visible wavelengths without substantially absorbing wavelengths of about 600 nm. As yet another example, if the desired resonant wavelength was about 570 nm to produce a yellow structural color, the spectrally selective absorbing components can absorb one or more other visible wavelengths without substantially absorbing wavelengths of about 570 nm. As yet another example, if the desired resonant wavelength was about 510 nm to produce a green structural color, the spectrally selective absorbing components can absorb one or more other visible wavelengths without substantially absorbing wavelengths of about 510 nm. As yet another example, if the desired resonant wavelength was about 475 nm to produce a blue structural color, the spectrally selective absorbing components can absorb one or more other visible wavelengths without substantially absorbing wavelengths of about 475 nm. As yet another example, if the desired resonant wavelength was about 445 nm to produce a indigo structural color, the spectrally selective absorbing components can absorb one or more other visible wavelengths without substantially absorbing wavelengths of about 445 nm. As yet another example, if the desired resonant wavelength was about 400 nm to produce a violet structural color, the spectrally selective absorbing components can absorb one or more other visible wavelengths without substantially absorbing wavelengths of about 400 nm.

As used herein, "without substantially absorbing the electromagnetic radiation near the resonant wavelengths" can mean a reduction in reflectance at the given resonant wavelength of no more than 0.2, or no more than 0.15, or no more than 0.1, or no more than 0.07, or no more than 0.05, no more than 0.01 or even less.

Generally, any spectrally selective absorbing components can be utilized, such as any plasmonic structures (either made of different materials, or having different sizes, or having different shapes) or semiconducting nanocrystal that display tailored absorption properties at the desired part of the visible spectrum and small enough sizes to fit into the interstitial sites of the photonic crystal. In certain embodiments, mixtures of different spectrally selective absorbing components can be utilized to tailor the desired combination of optical properties and size. In certain embodiments, the wavelengths that are selectively absorbed or the extent of the absorption can be changed based on the size or shape of the spectrally selective absorbing components, or their chemical composition.

In some exemplary embodiments, some suitable spectrally selective absorbing components included spherical gold nanoparticles with a size from 5 nm-80 nm, which do not significantly absorb at 650 nm but selectively absorb other visible wavelengths to create red structural color. Changing the size of gold spheres within and beyond this range allows to further tune their absorptive properties.

In other exemplary embodiments, other suitable spectrally selective absorbing components such as gold rods having a short axis diameter of 10 nm, a long axis length of 50-60 nm and an aspect ratio of 5-6 were used. Such nanoparticles can have an absorbing wavelength that is centered around 520 nm and 1000 nm with an absorption minimum centered around about 620 nm. Such nanoparticles can be utilized to prepare orange-red to brown color. Changing the size and the aspect ratio of gold nanorods beyond this range allows to further tune their absorptive properties.

Some other suitable spectrally selective absorbing components include gold hollow spheres that can be tuned for all wavelengths depending on shell thickness and core diameter. For example, gold hollow sphere having a core diameter of 600 nm and a shell of 7 nm can have an absorbing wavelength centered at around 910 nm with an absorption minimum below 650 nm, which would be suitable for producing a green color. Changing the size of the sphere and the thickness of the shell allows to further tune their absorptive properties Some other suitable spectrally selective absorbing components include silver nanoplates having a diameter of 40-50 nm and a thickness of 10 nm. Such nanoparticles can have an absorbing wavelength centered around 550 nm with an absorption minimum centered around 450 nm and above 700 nm, which would be suitable for producing a purple/red color.

Some other suitable spectrally selective absorbing components include silver nanoplates having a diameter of 60-80 nm and a thickness of 10 nm. Such nanoparticles can have an absorbing wavelength centered around 650 nm with an absorption minimum below around 480 nm, which would be suitable for producing a blue color.

Some other suitable spectrally selective absorbing components include silver nanoplates having a diameter of 110-150 nm and a thickness of 10 nm. Such nanoparticles can have an absorbing wavelength centered around 950 nm with an absorption minimum centered around 520 nm, which would be suitable for producing a green color. Changing the size and thickness of the plate beyond the specified dimensions allows to further tune their absorptive properties In certain embodiments, the spectrally selective absorbing components (e.g., metal nanoparticles) described herein can be capped with a shell material to allow more homogenous distribution in the photonic crystal. For example, the shell material can include material (e.g., silica) that has an affinity with the photonic crystal material (e.g., silica), which can provide improved dispersion throughout the photonic crystal as shown in FIG. 3D. Also, organic capping layers and ligand shells can be used to optimize incorporation and dispersability in the matrix. These include but are not limited to organic thiol compounds, pegylated thiol compounds, citrates and related chemical compounds, negatively and positively charged surfactants, cetyl-trimethylammonium bromide and related chemical compounds, carboxylic acids, phosphates and others.

Other spectrally selective absorbing components, such as core-shell complex metal nanoparticles, metal nanorods having two different metals, mixtures of different spectrally selective absorbing components, and the like can be utilized. Any other type of spectrally selective absorbing nanostructure can be used. These include but are not limited to gold nanoparticles of shapes and sizes beyond those mentioned, silver nanoparticles of shapes and sizes beyond those mentioned, copper nanoparticles of different shapes and sizes, aluminum nanoparticles of any size and shape, inorganic semiconductor nanoparticles with any size and shape.

Fabrication

Two exemplary fabrication techniques to create the photonic crystal particulates containing spectrally selective absorbing components are described herein. However, other embodiments are within the scope of the present disclosure. These include but are not limited to emulsification techniques leading to the formation of discrete droplets of a mixture that forms a photonic particle dispersed in a continuous phase, spray drying, spin coating, doctor blading, evaporative assembly in combination with removing the thin films of photonic films to form particles and mechanical grinding of particles into desired shapes or forms.

A. Emulsion Technique

Figures 3A, 3B, 3C:
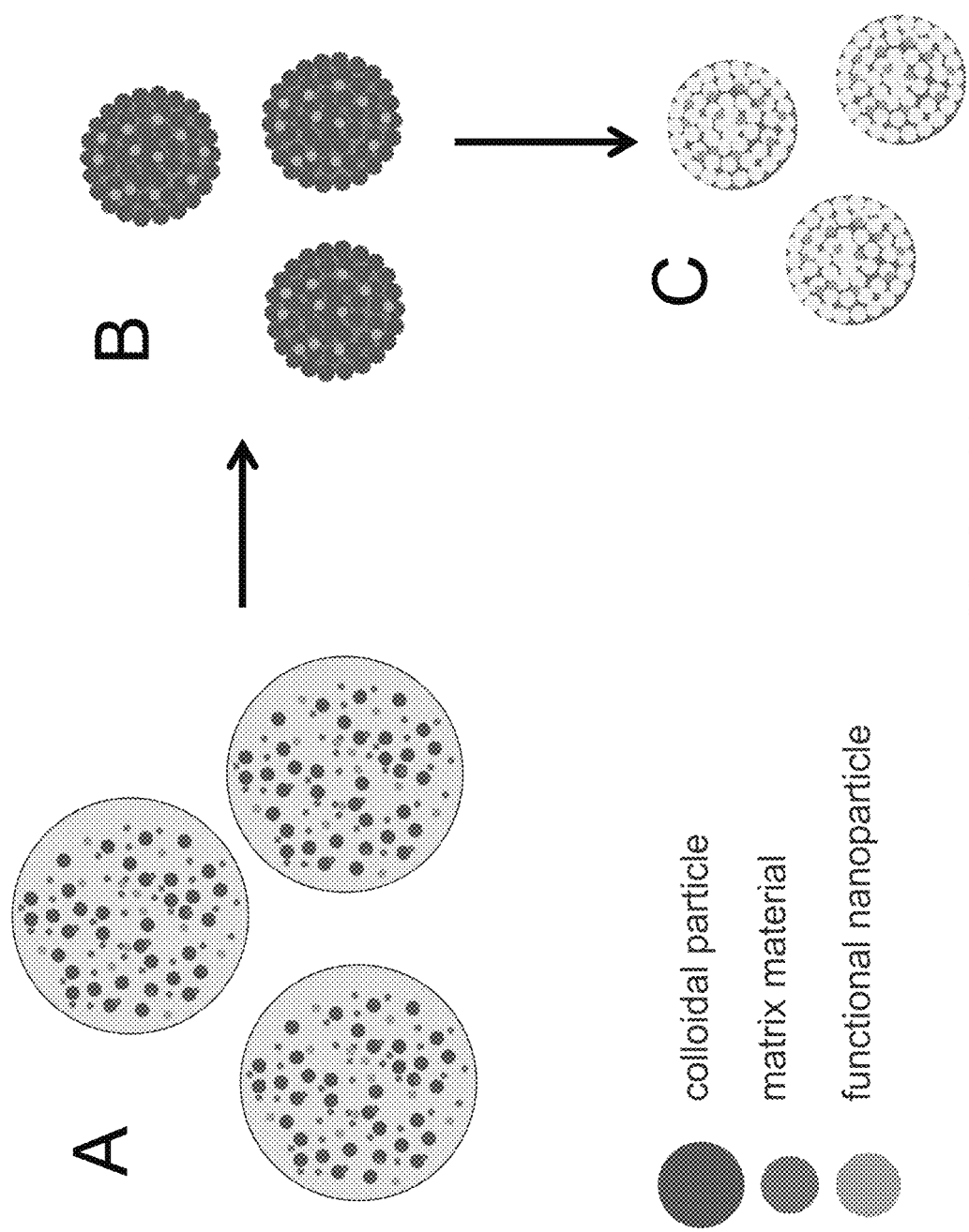
FIGS. 3A-3C provide a schematic illustration of forming spherical photonic crystal particles having spectrally selective absorbing components in accordance with certain embodiments.
Figure 3D:
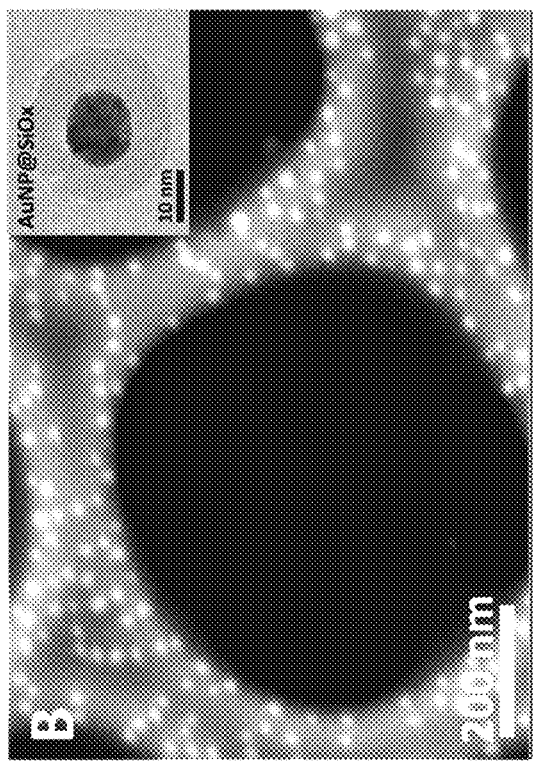
FIG. 3D demonstrates that a more homogeneous distribution of gold nanoparticles can be obtained if the nanoparticle shells are coated with silica when dispersed in a photonic crystal having a silica matrix in accordance with certain embodiments.

FIGS. 3A-3C schematically shows an exemplary fabrication process of spherical photonic crystal particulates containing gold nanoparticles as the spectrally selective absorbing component. As shown, FIG. 3A shows a schematic illustration of an aqueous dispersion of polymer colloid particles and nanoparticles confined within an emulsion droplet. Each droplet is surrounded by an oil environment. In certain embodiments, each droplet can contain a matrix material chosen to be surrounding the colloidal particles and the nanoparticles after crystallization. In certain embodiments, a surfactant (not shown) can be utilized to stabilize the emulsion. Then, as shown in FIG. 3B, evaporation or removal of water into the oil phase can induce self-assembly of the colloidal particles into a photonic crystal. During the evaporation or removal, the nanoparticles are deposited into the interstitial sites of the polymer colloid particles. Additionally, if a matrix material is present, it will be deposited into the interstitial sites as well and forms an interconnected network. Then, if desired, as shown in FIG. 3C, the colloidal particles can be used as sacrificial material and be removed (e.g., by thermal combustion or by dissolution in a solvent for the applied polymer, such as tetrahydrofuran, toluene or the like if polymethylmethacrylate (PMMA) or polystyrene (PS)colloids are used; or hydrogen fluoride if silica colloids are used) to increase the dielectric contrast within each photonic crystal particle. Numerous different sacrificial material can be utilized, such as polystyrene (PS) colloidal particles, silica particles, acrylate particles, alkylacrylate particles, substituted alkylacrylate particles, poly(divinylbenzene) particles, polymers, random copolymers, block copolymers, dendritic polymers, supramolecular polymers, or combinations thereof.

Figure 3D:
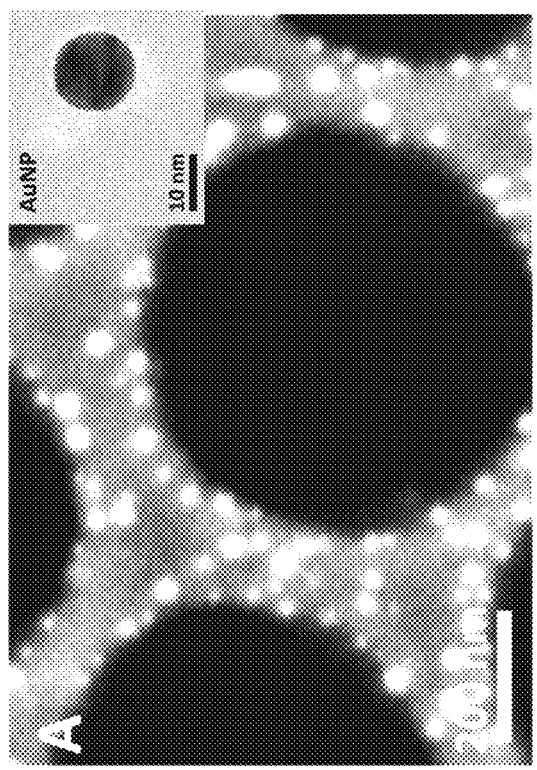
Figure 4:
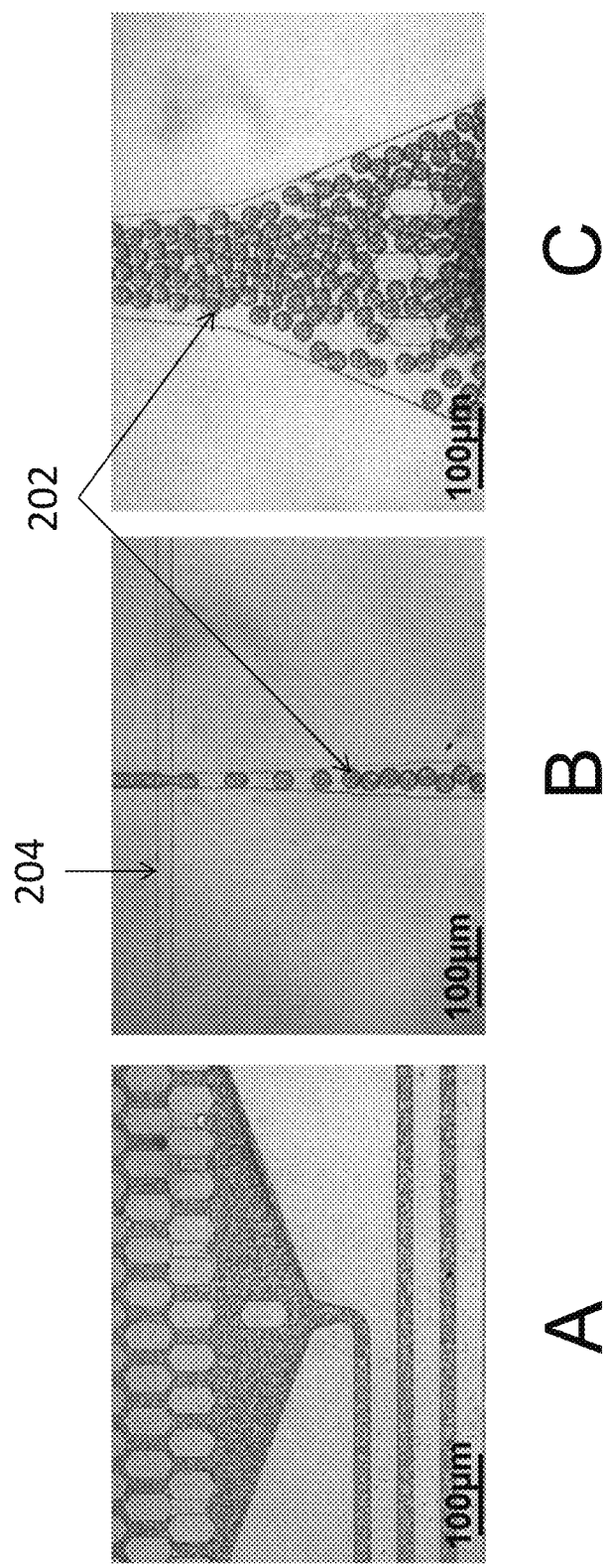
FIG. 4 shows images of forming spherical photonic crystal particles in accordance with certain embodiments.

FIG. 4 shows an exemplary microfluidic device that can be used for the generation of emulsion droplets described in FIG. 3. As shown in FIG. 4A, colloidal dispersion, containing polymer colloid particles and nanoparticles in water can be passed through the device. Thereafter, as shown in FIG. 4B, the emulsion droplets 202 can be formed by a cross-flow of oil 204 used as continuous phase to yield emulsion droplets (which can be highly monodisperse), which can be collected as shown in FIG. 4C.

Figure 5:
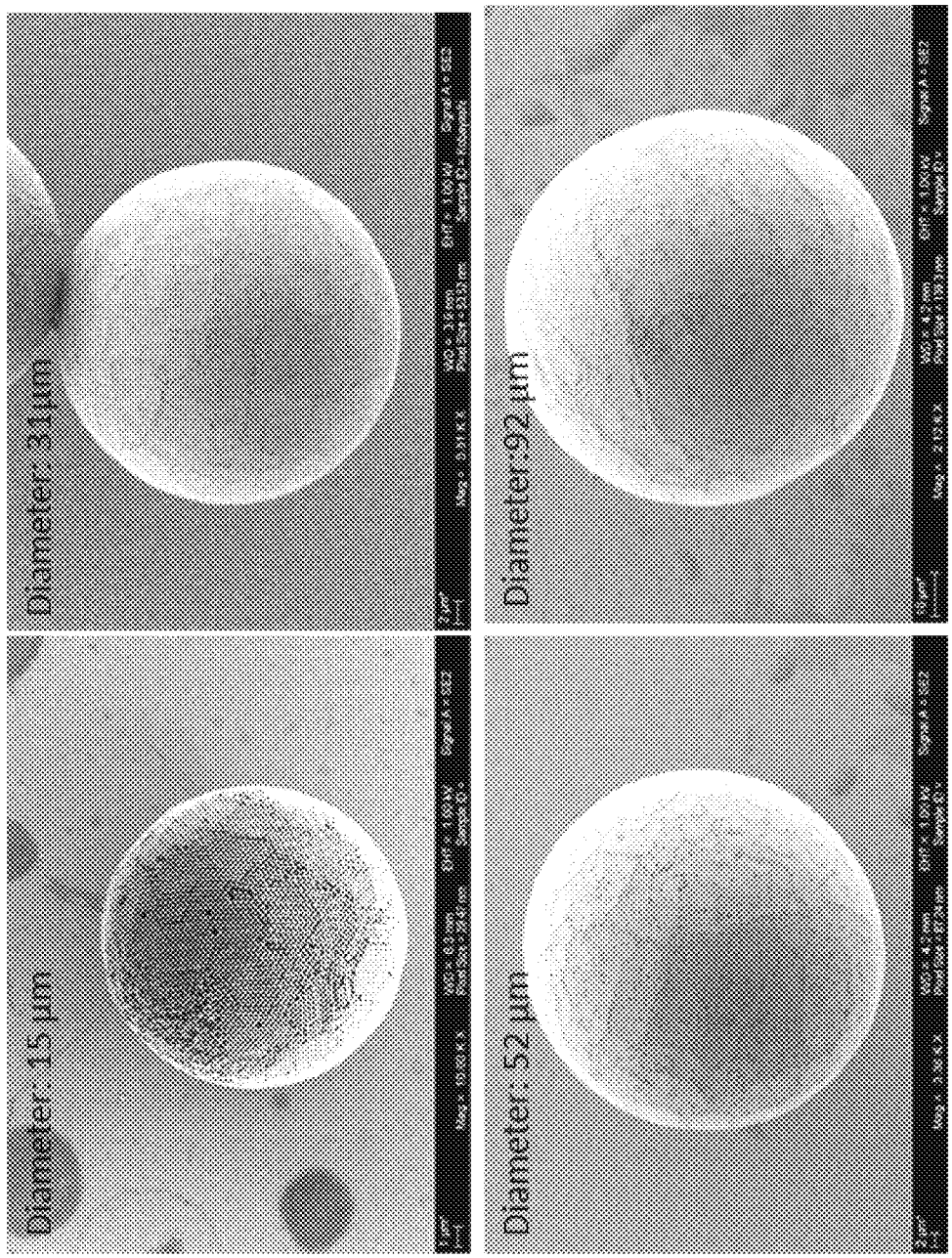
FIG. 5 shows scanning electron microscopy images (SEM) of some exemplary spherical photonic crystal particles of different sizes in accordance with certain embodiments.

The size of the spherical photonic crystal particles having spectrally selective absorbing components can be precisely tailored by adjusting the concentration of colloidal particles in the dispersion, by the size of the microfluidic cross junction and by changing the flow rates in the device. FIG. 5 demonstrates the control over the size of the spherical photonic crystal particles prepared from 0.5, 1 and 2 wt. % of a colloidal dispersion using a 50 μm wide cross junction or oil. Although absorbing nanoparticles were not utilized in FIG. 5, the example clearly demonstrates the control over the size of the spherical photonic crystal particles that can be formed.

Figure 6:
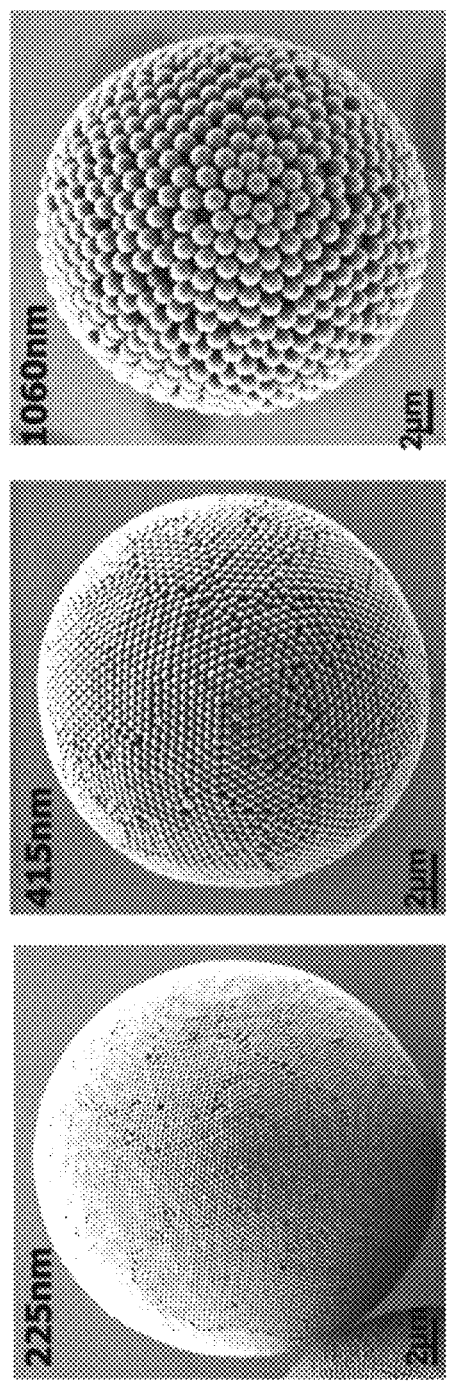
FIG. 6 shows SEMs of some exemplary same-size spherical photonic crystal particles composed of colloids of different sizes in accordance with certain embodiments.

Moreover, differently-sized colloidal particles can be utilized to produce such spherical photonic crystal particles. As shown in FIG. 6, approximately same sized spherical photonic crystal particles can be formed using differently sized colloidal particles.

Figure 7:
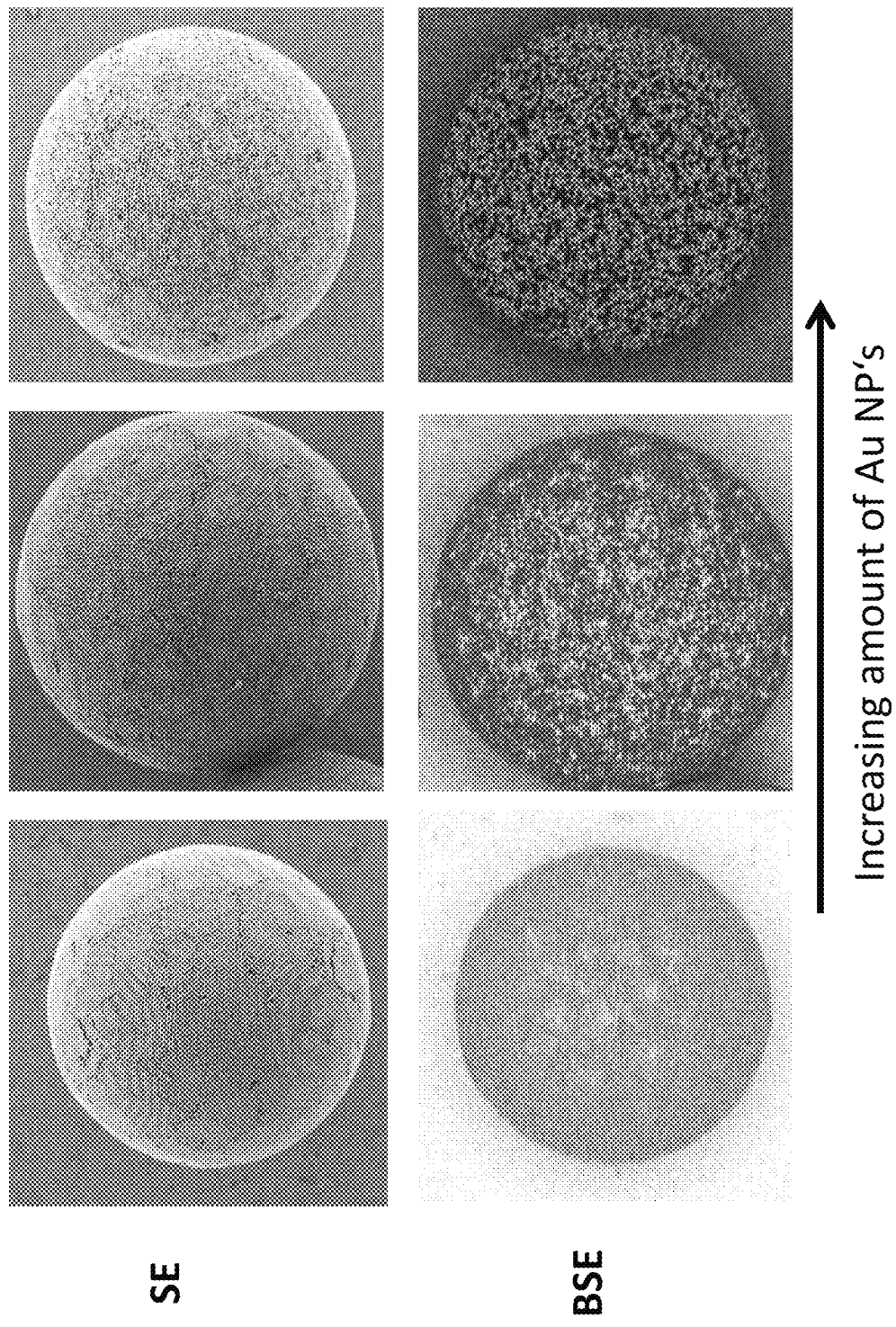
FIG. 7 shows SEMs of spherical photonic crystal particles having gold nanoparticles incorporated therein in accordance with certain embodiments.

In certain embodiments, spherical photonic crystal particles can be fabricated using colloidal particles and a spectrally selective absorbing component. FIG. 7 shows images of spherical photonic crystal particles having increasing amounts of gold nanoparticles. The top row shows scanning electron images of the produced particles using secondary electrons (SE), that show topography of the surface. The bottom row shows scanning electron images of the produced particles using backscattered electrons that show differences in composition, where gold nanoparticles appear brighter.

Figure 8A:
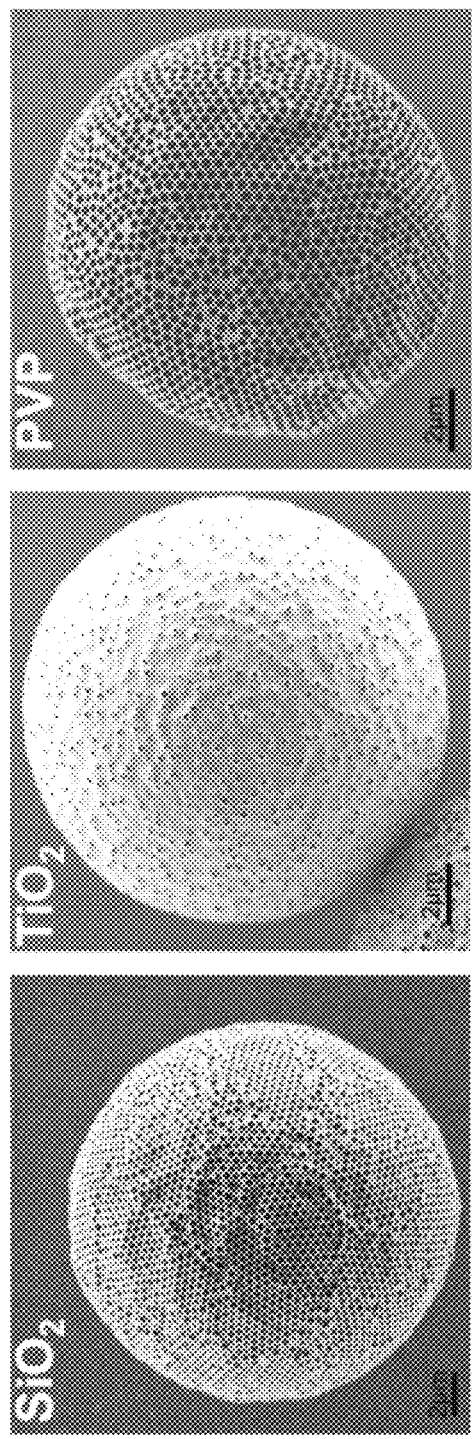
FIGS. 8A show SEMs of some exemplary inverted spherical photonic crystal particles and 8B shows a cross-section of such inverted spherical photonic particle in accordance with certain embodiments.
Figure 8B:
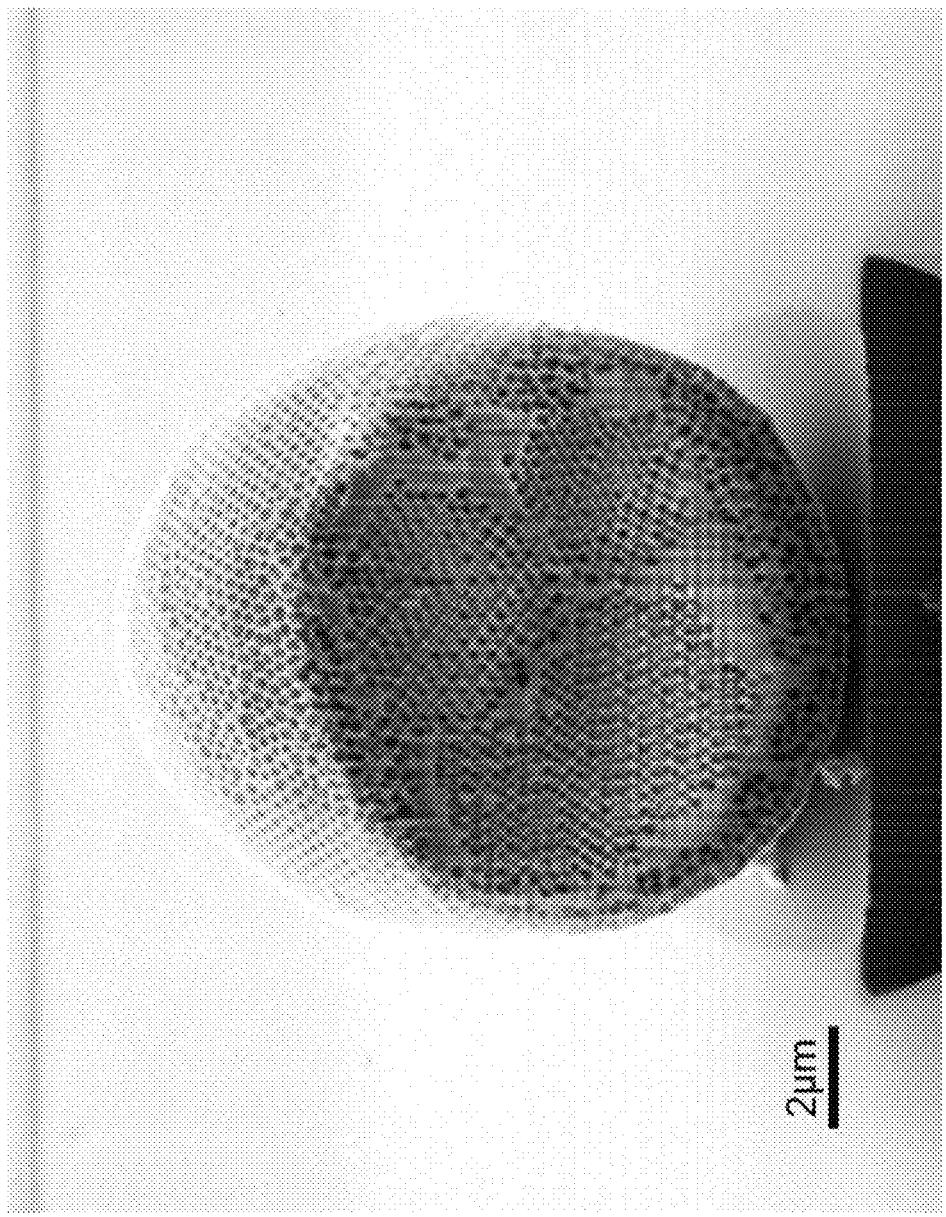

In certain embodiments, addition of a matrix material, or a precursor to a matrix material, can be utilized to generate an inverse structure as the photonic crystal structure. As shown in FIG. 8A, the addition of a second material to occupy the interstitial sites has been used to create inverse opal microspheres with an inorganic matrix (silica and titania) and a polymeric matrix consisting of water soluble poly(vinyl-pyrrolidone). FIG. 8B shows a cross-section of such an inverse structure showing the high degree of internal order.

B. Sacrificial Mold Technique

In certain embodiments, the photonic crystal particle having spectrally selective absorbing components can be fabricated using a sacrificial photoresist method. The exemplary embodiment described here provides the ability to obtain high amounts of photonic crystal particles with nearly 100% yield.

Figure 9:
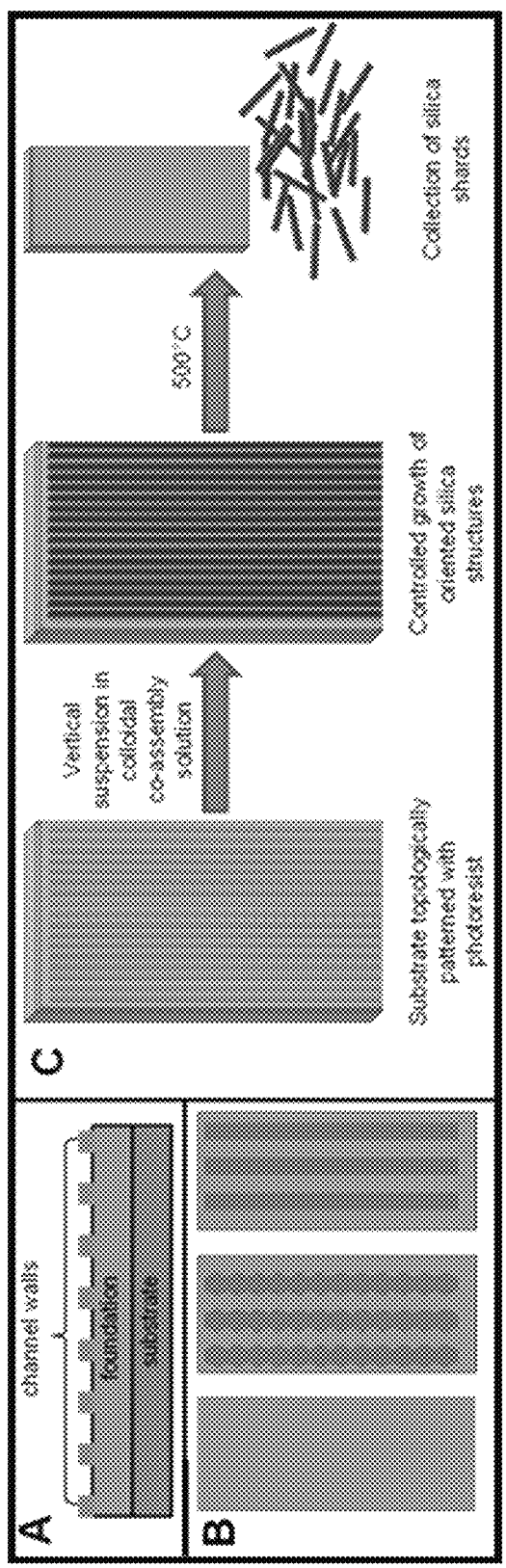
FIG. 9 shows a schematic illustration of forming elongated photonic crystal particles in accordance with certain embodiments.

As schematically illustrated in FIG. 9A, a substrate can be overlaid with a sacrificial layer, such as a photoresist, identified as "foundation." In certain embodiments, the "foundation" can be patterned, such as forming pits, divots, inverted pyramids, and the like.

Thereafter, channel walls can be formed using a similar sacrificial material, such as a photoresist. Any desired pattern of the channel walls can be produced, with three exemplary structures shown in FIG. 9B. In certain embodiments, the channel walls can be partitioned so that the empty spaces form discrete regions, such as bricks, cubes, and the like.

Then, as shown in FIG. 9C, colloidal particles, the spectrally selective absorbing component, and optionally a matrix material or precursor thereof, can be introduced within the channels and allowed to order. Thereafter, the channels can be removed to obtain a collection of photonic crystal particles (e.g., flakes, shards, . . . ) having spectrally selective absorbing components. In certain embodiments, by applying a high temperature treatment, removal of the sacrificial materials, removal of the polymeric colloidal particles, and conversion of the matrix material into a high dielectric material can be obtained in one step.

Figure 10:
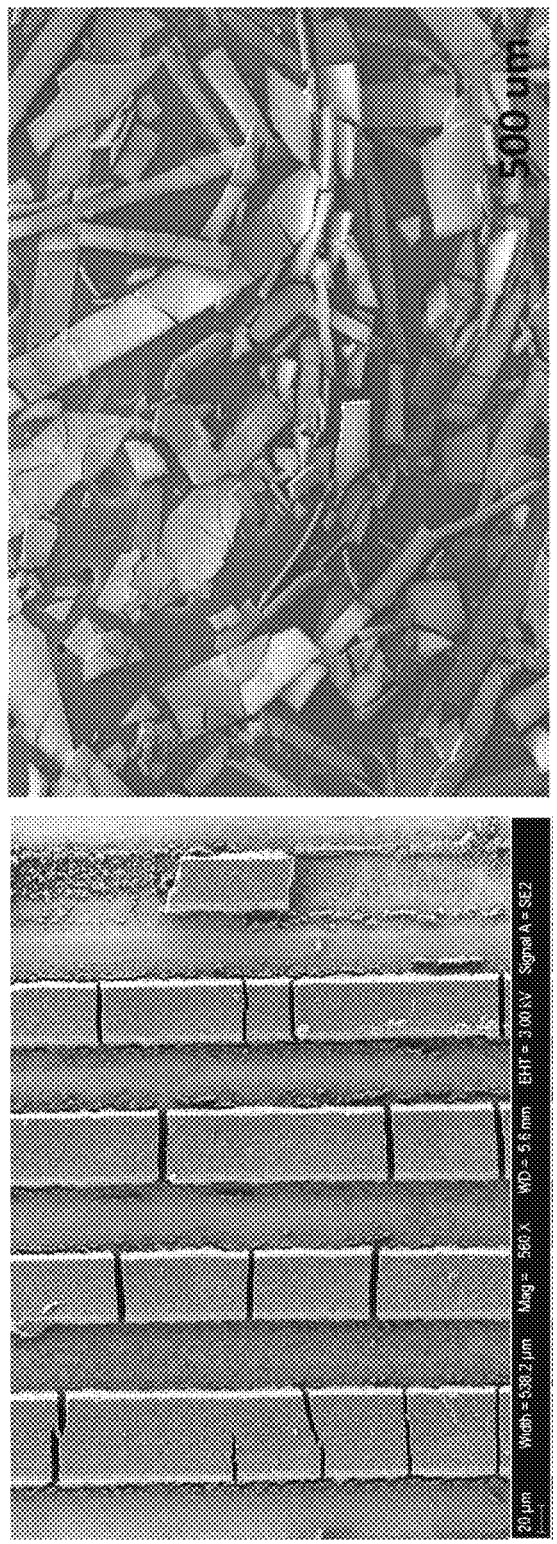
FIG. 10 shows SEM images of exemplary elongated photonic crystal particles having spectrally selective absorbing components in accordance with certain embodiments.

Some exemplary structures obtained by the sacrificial mold technique are shown in FIG. 10. FIG. 10A shows that the photoresist channels define the photonic crystal particle sizes in two dimensions (height and width) while natural cracking can induce the third dimension (length) at random. As shown in FIG. 10B, a high yield can be obtained. Other embodiments are possible using sacrificial molds of arbitrary geometry and pit structure. For example, the photoresist channels can define an interconnected honeycomb structure that preferentially breaks at the neck points.

Figure 11:
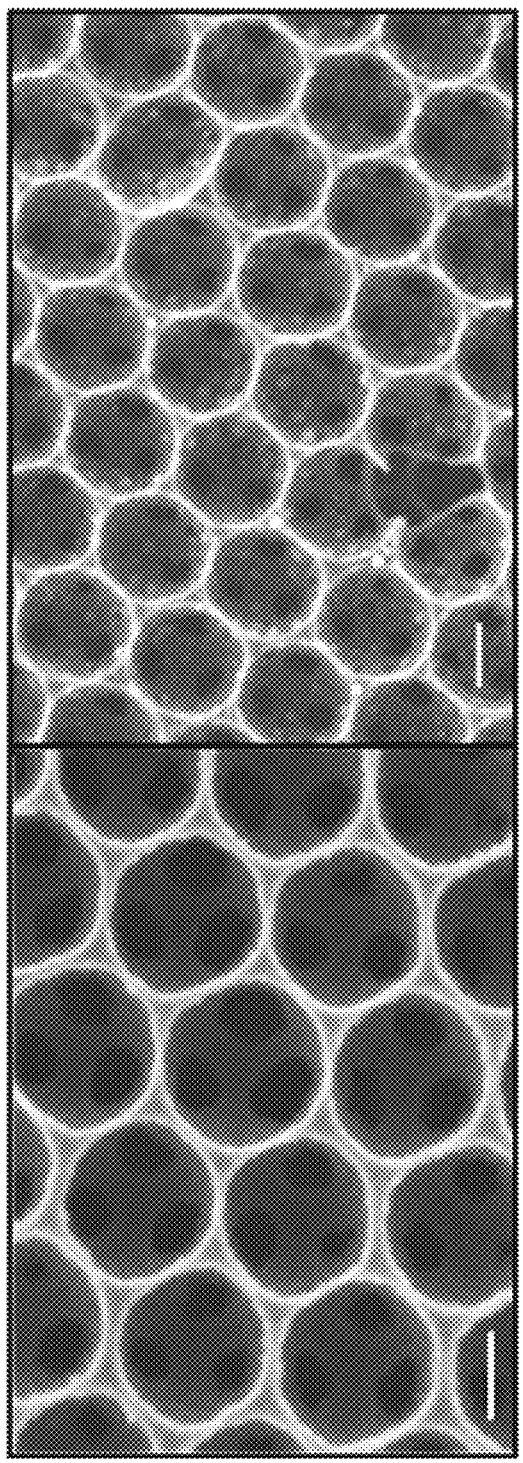
FIG. 11 shows SEM images of an exemplary inverse opal photonic particle having gold nanoparticles (AuNPs) embedded therein in accordance with certain embodiments.

Following the sacrificial mold fabrication technique described herein, photonic crystal particles having spectrally selective absorbing components were fabricated. In addition to the colloidal particles and the matrix elements in the initial dispersion solution (0.05%-0.1% solid content), very low amounts of gold nanoparticles, AuNP (11.8 nm±0.4), were added. This resulted in a total concentration of gold nanoparticles ranging from 10 to approximately 100 nanomoles/L in the assembly solution. FIG. 11 shows SEM images of cross-sections of such inverse opal structures without gold nanoparticles (left) and inverse opal structure having gold nanoparticles within each photonic crystal particle (right). Plasmonic resonance from these particles imparts a red color previously difficult to achieve by interference structural pigments in simple, scalable and cost-efficient procedures.

Figures 12A, 12B:
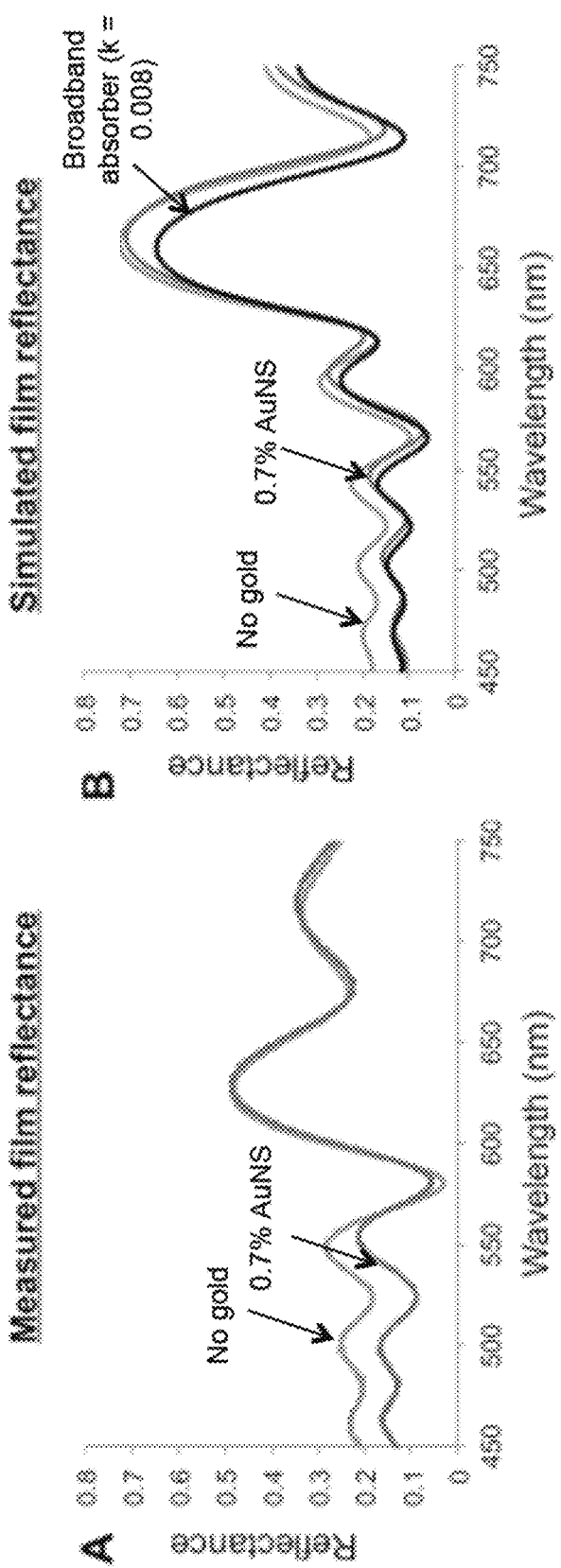
FIG. 12A shows the comparison of the normal-incidence reflectance spectra of substrates covered with photonic crystal particles with and without AuNPs incorporated therein in accordance with certain embodiments.
FIG. 12B shows simulations showing the effect of AuNP doping on the reflectance spectrum (normal incidence) of inverse-opal photonic crystals in accordance with certain embodiments.

As shown in FIG. 12A, comparison of the normal-incidence reflectance spectra of substrates covered with photonic crystal particles with and without AuNPs contained therein shows suppression of the short-wavelength regions of the visible spectrum by the AuNPs. Both samples have a thickness of 10 close-packed layers on a silicon substrate, however, one sample is without gold doping while the other sample contains 0.7% by solid volume of gold nanoparticles. As shown, the resonant wavelength at about 620 nm remains unchanged while the other wavelengths below 620 nm are selectively reduced in intensity with the addition of gold nanoparticles.

FIG. 12B shows a simulation study of the effect of AuNP doping on the reflectance spectrum (normal incidence) of inverse-opal photonic crystals, where suppression of the short-wavelength regions of the spectrum is observed with minimal effect on the resonance peak. FIG. 12B also simulates the effect of a broadband absorber on the reflectance spectrum and shows that the intensity of the reflected light at the resonance wavelength is reduced.

Figure 12C:
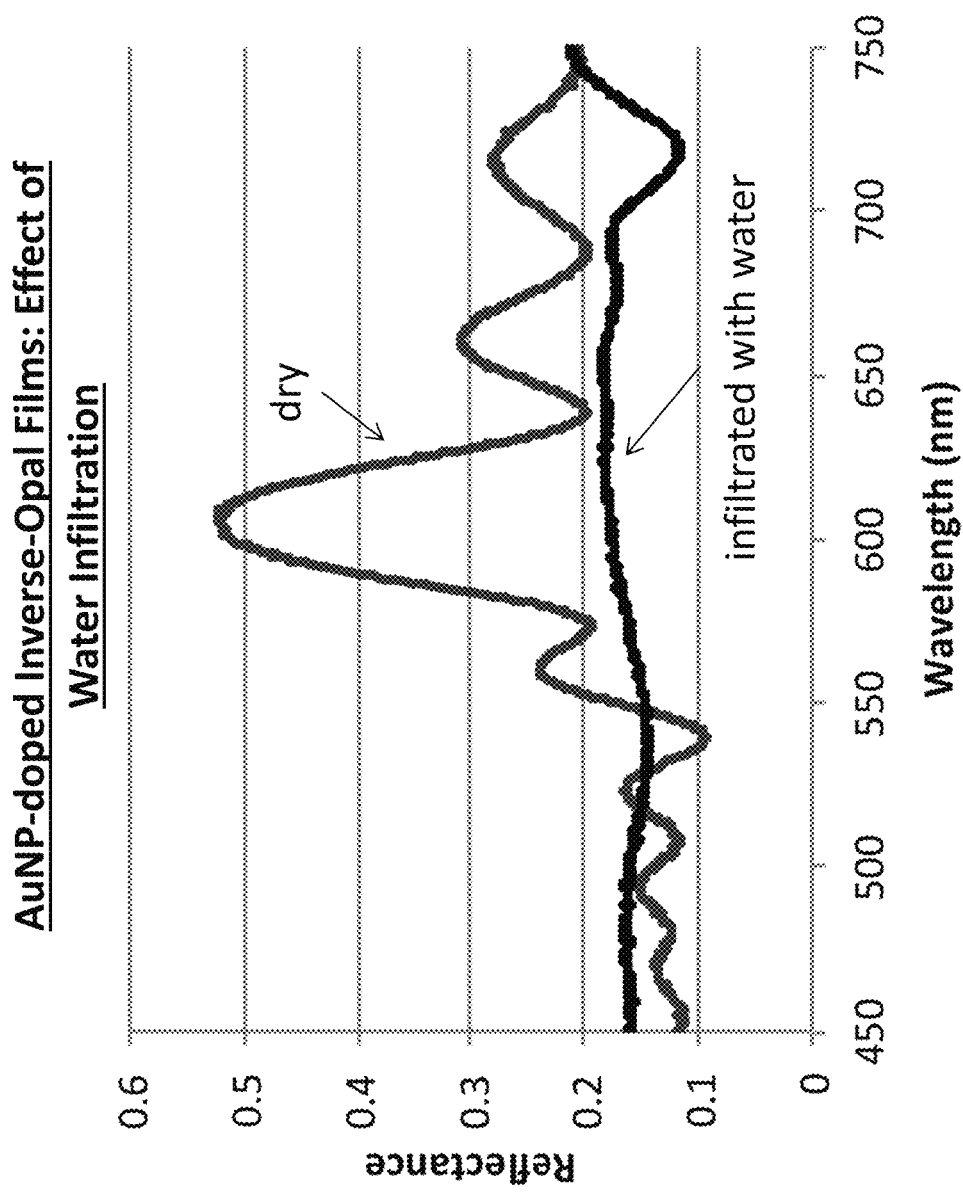
FIG. 12C shows reflectance of an AuNP-doped inverse-opal film (made of silica) before and after water infiltration in accordance with certain embodiments.

Infiltrating AuNP-loaded photonic crystal particles with water has a significant effect on the reflectance spectra characterized by the elimination of wavelength-scale manipulation by the 3D porous crystal. FIG. 12C shows reflectance of a AuNP-doped inverse-opal film (made of silica) showing the effect of water infiltration. As shown, when the resonant wavelength of the photonic crystal disappears due to the introduction of water, the bright red structural color is no longer observed.

Figure 12D:
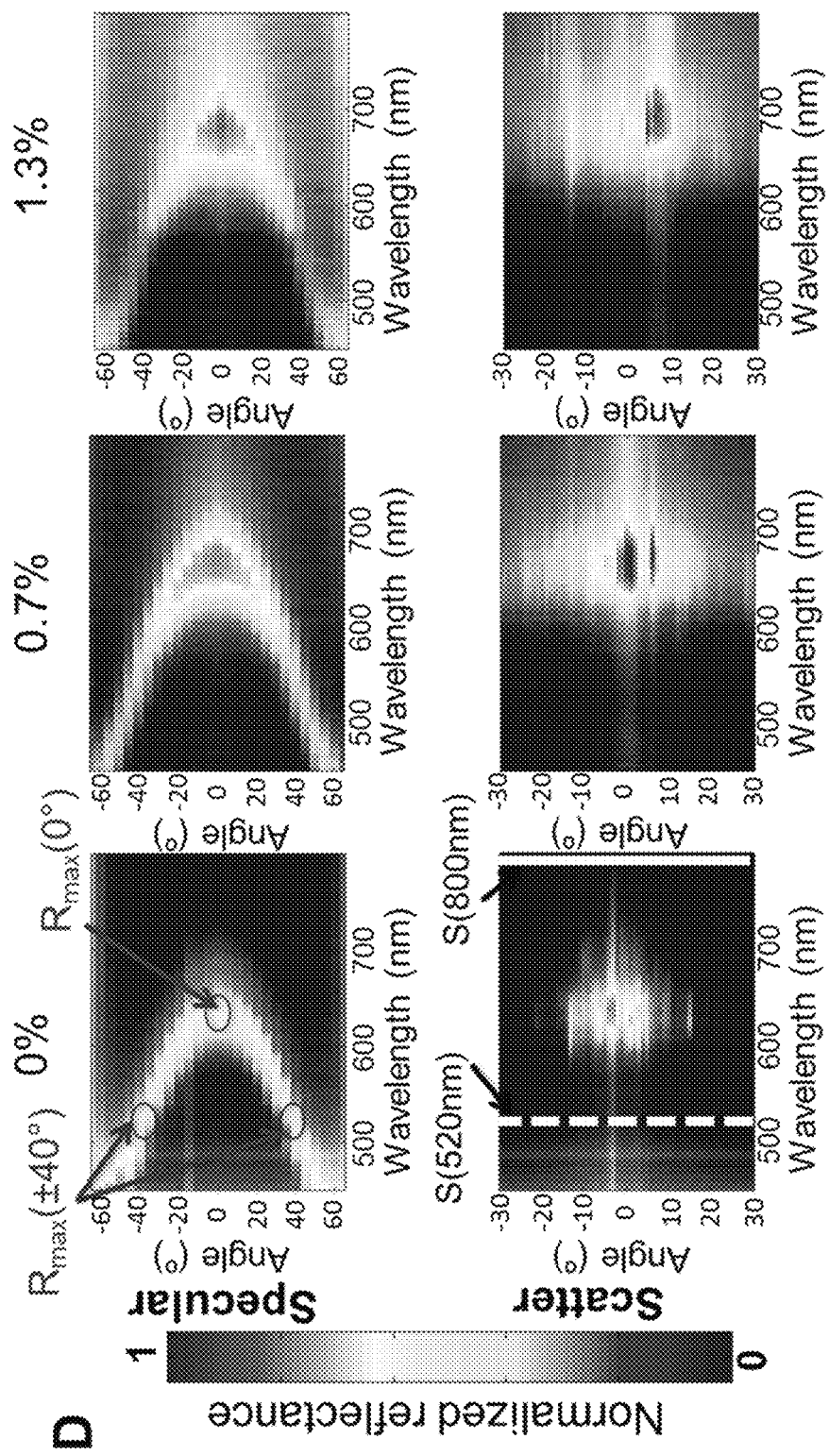
FIG. 12D shows specular reflectance and scattering for a surface covered with inverse opal photonic crystals without AuNPs and with AuNPs incorporated therein in accordance with certain embodiments.

FIG. 12D shows a normalized specular reflectance (top row) and diffuse scattering (bottom row, 0° illumination) of the photonic bricks with gold nanoparticle concentrations of 0%, 0.7% and 1.3% by solid volume. As shown, more pronounced reflectance of red colors and less reflectance of the shorter wavelengths for the photonic crystal particles containing AuNPs is observed over multiple angles due to the selective absorption of gold nanoparticles.

The composition of the matrix can be controlled using sol-gel precursors or by adding nanoparticles to the precursors. For molecular precursors, the precursor can be pre-hydrolyzed and then added to the assembly solution for the co-deposition of the colloids, spectrally selective absorber, and the matrix. For instance, for silica, the molecular precursor tetraethyl orthosilicate (TEOS) can be pre-hydrolyzed in an ethanolic solution with 0.1M HCl (1:1:1.5 by mass of TEOS:0.1M HCl:EtOH) for one hour.

Figure 13:
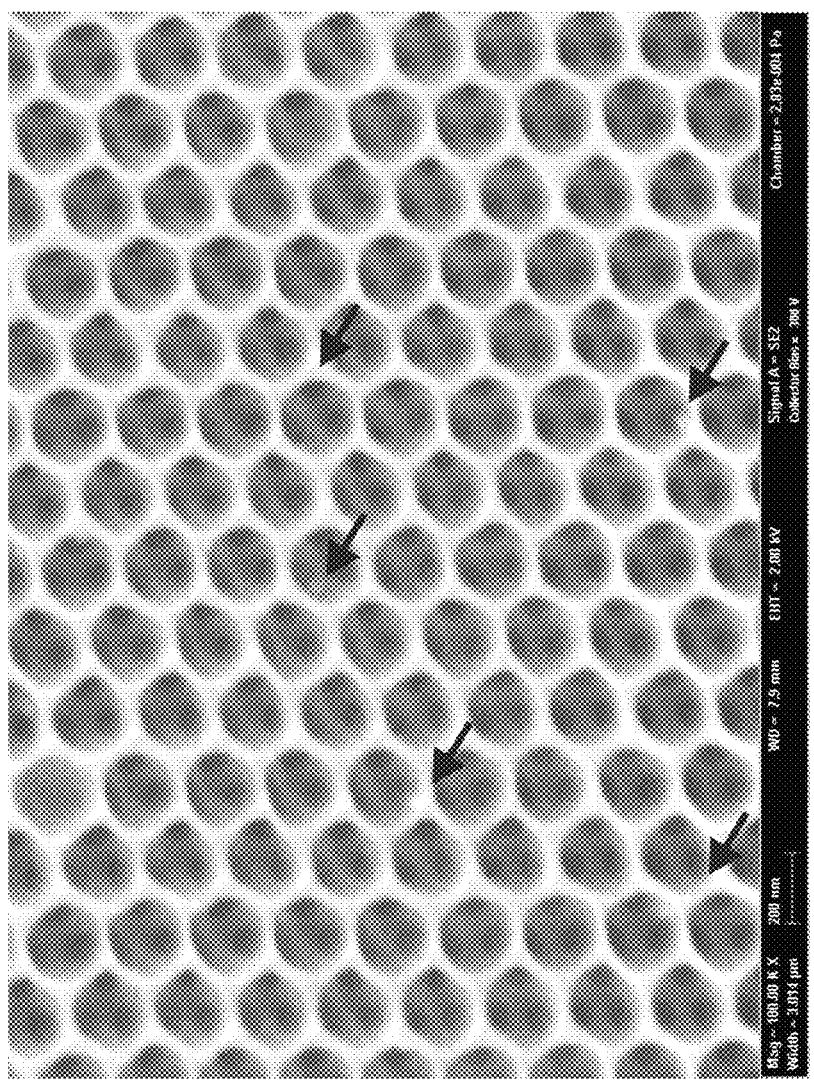
FIG. 13 shows photonic crystal particles made using titania in accordance with certain embodiments.

FIG. 13 shows some other exemplary photonic crystal particles containing spectrally selective absorbing components produced according to the sacrificial mold technique but using titania as matrix material. Photonic crystal particles were fabricated by hydrolyzing titanium bis(ammoniumlactato)dihydroxide precursors for five hour under acidic conditions and then placing the hydrolyzed solution in a co-assembly solution together with colloids to fabricate photonic crystal particles having titania. Co-assembly solution refers to bulk water-based solution of colloidal suspension, precursors, and nanoparticles (e.g., gold) that can serve as spectrally selective absorbing components. The substrate is vertically suspended in the co-assembly solution for deposition of the colloid and sol-gel matrix. Assembly is performed on a structured substrate with a foundation layer as for the silica-based photonic particles described above. The gold nanoparticles are shown in arrows.

Mixtures of different materials can be utilized to form photonic crystal particles. For instance, the composition of the structure can be controlled using sol-gel precursors or by adding nanoparticles to the precursors. For molecular precursors, the precursor can be pre-hydrolyzed and then added to the assembly solution for the co-deposition of the colloids and the matrix. For instance, for silica, the molecular precursor tetraethyl orthosilicate (TEOS) can be pre-hydrolyzed in an ethanolic solution with 0.1M HCl (1:1:1.5 by mass of TEOS:0.1M HCl:EtOH) for one hour. Further, the matrix precursors can be added in any combination to achieve mixed matrix materials, for instance silica-titania hybrid photonic crystal particles shown in FIGS. 14A-14C. Regardless of the matrix material, the required amount of precursor is added to a solution with the templating spheres in a high enough concentration to form a continuous film.

Figures 14A, 14B, 14C:
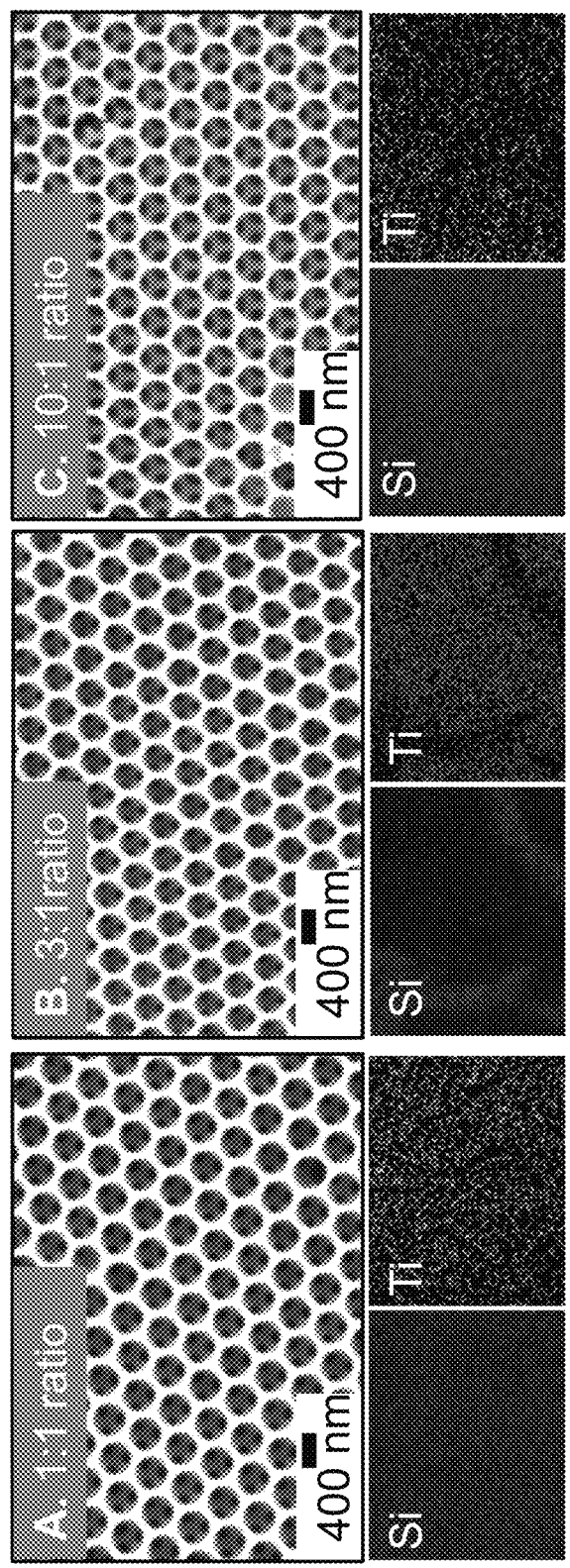
FIGS. 14A-14C shows photonic crystal particles made using a mixture of silica and titania in accordance with certain embodiments.

For titania, the sol-gel chemistry can be controlled by using titania-alkoxides and either adding a chelating ligand such as lactic acid, or using a water-stable precursor such as titanium bis-ammoniumlactatodihydroxide (TiBALDH), or using an ethanolic assembly solution. Photonic particles made with TiBALDH added to an aqueous assembly solution are shown in FIGS. 14A-14C. In addition to molecular precursors, silica, titania or other transition metal nanoparticles can be used as a part of the matrix material.

As shown in FIGS. 14A-14C, photonic crystal particles were fabricated as described above, except tetraethylorthosilicate (TEOS) and titanium bis(ammoniumlactato)dihydroxide (TiBALDH) precursors, in the ratios indicated, were hydrolyzed individually for 1 hour under acidic conditions before being placed in the co-assembly solution to achieve a composite structure made of silica and titania. The top row shows SEM images showing the high degree of order that can be achieved. Energy Dispersive X-ray Spectroscopy (EDS) maps are shown at the bottom row to confirm presence of silicon and titanium. All hybrid films contain both silica and titania. Further elemental analysis with X-ray Photoelectron Spectroscopy (XPS) confirms both silica and titania phases in the structure, depending on the amount of each precursor added.

C. Functionalization

Figure 15:
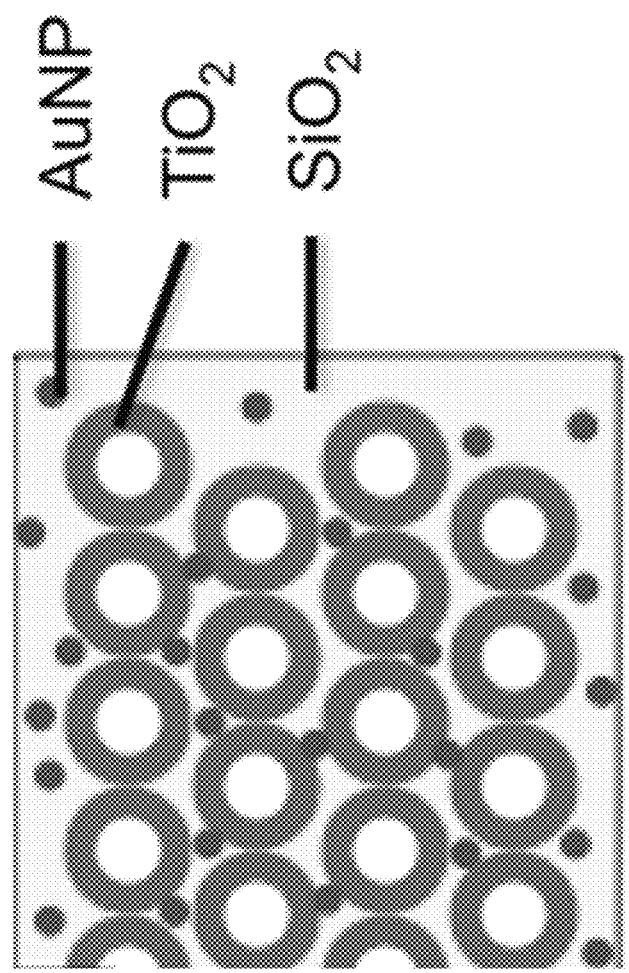
FIG. 15 shows a schematic illustration on coating the pores of the photonic crystal particles with titania in accordance with certain embodiments.

Adding to the multi-faceted tunability of these photonic crystal particles having spectrally selective absorbing components, the photonic crystal particles can be functionalized or coated with varying surface chemistries. The additional chemistries can provide additional desired properties, such as UV protection properties, antimicrobial properties, anti-inflammatory properties, controlled release of desired molecules, photocatalytic properties or combinations thereof. FIG. 15 shows a schematic illustration of surface functionalization of the pores of the photonic crystal particles. For example, the pores of the photonic crystal particles made with silica and gold nanoparticles can be coated with titania, which can provide additional photocatalytic properties.

Figure 16A:
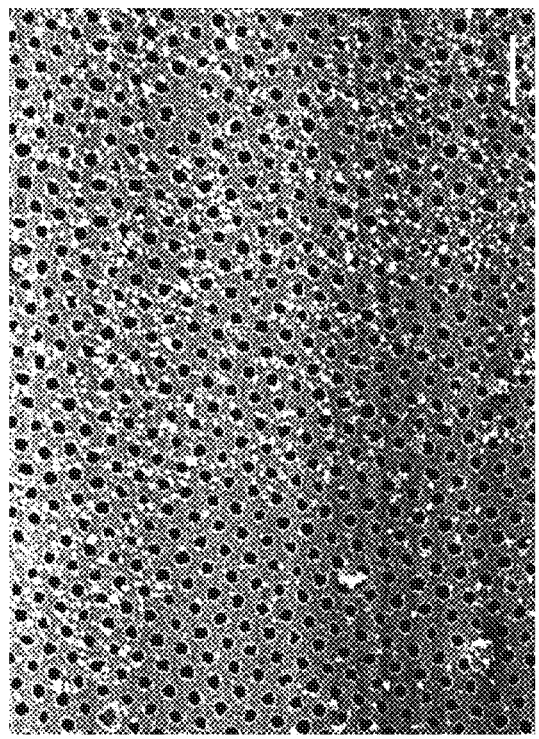
FIGS. 16A and 16B show SEM and energy dispersive x-ray spectroscopy (EDS) images of titania-coated photonic crystal particles in accordance with certain embodiments.
Figure 16B:
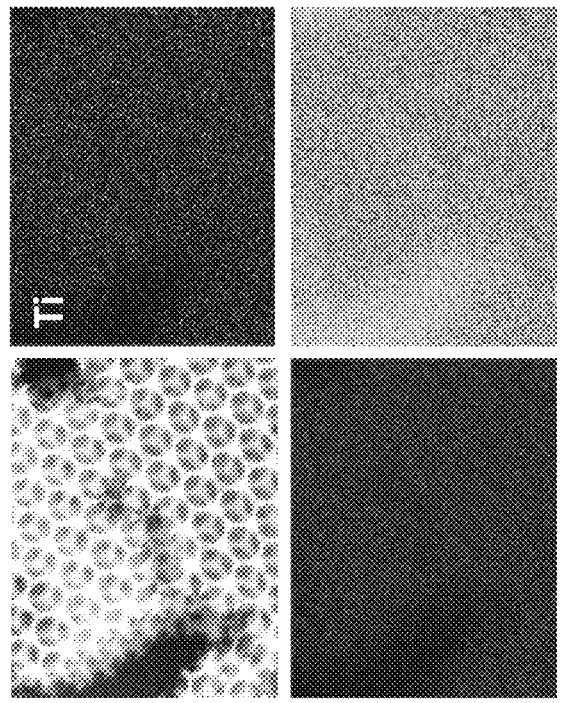

Various different functionalization procedures can be envisioned. For example, in order to provide a surface property that is compatible in certain application like cosmetics, the photonic crystal particle can be coated with regulatory approved material. For instance, FIGS. 16A and 16B show photonic crystal particles having silica conformally coated with titania layer using atomic layer deposition (ALD). The precursors that were used for ALD were tetrakis (dimethylamido)titanium (TDMAT) and water. Other precursors leading to titania thin films in ALD processes can be used as well. The process was carried out at 100° C. and TDMAT and water were sequentially deposited for a duration of 100 cycles whereby one cycle includes 0.02 s of TDMAT followed by 30 s of wait time for the precursor to dissipate followed by 0.02 s of water followed by another 30 s of wait time. ALD or chemical vapor deposition (CVD) techniques can allow controlled deposition of a second matrix material to an inverse opal photonic particle such as titania in a defined way so that it forms a film covering the inner matrix material completely. Alternatively, ALD can be used on a direct opal structure particle to obtain an inverse opal particle composed of titania.

FIG. 16A shows SEM and energy dispersive x-ray spectroscopy maps of ALD titania-coated silica inverse opal. Titanium signal is observed in the EDX signal indicating the presence of titania. FIG. 16B shows backscattered SEM image of a silica inverse opal photonic crystal particle containing gold nanoparticles coated with titania. Bright spots indicate presence of gold nanoparticles. Visual inspection of the photonic crystal particles before and after ALD coating of titania showed a slight change in the optical properties to a darker red color.

In certain embodiments, functionalization can be carried out to produce a desired change in the structural color due to certain stimuli. For example, the surfaces of the photonic crystal particles can be functionalized to provide an affinity to particular types of material so that infiltration of the material leads to a change in the structural color. This affords a novel approach to producing dynamic wettability in response to different liquids. For example, covalent bonding of functional groups through silane chemistry can be carried out. As another example, ionic bonding of an acrylic-acidbased polyelectrolyte monolayer containing an azobenzene chromophore, whose wetting properties can be tuned by photobleaching, can be carried out.

Figures 17A, 17B, 17C, 17D:
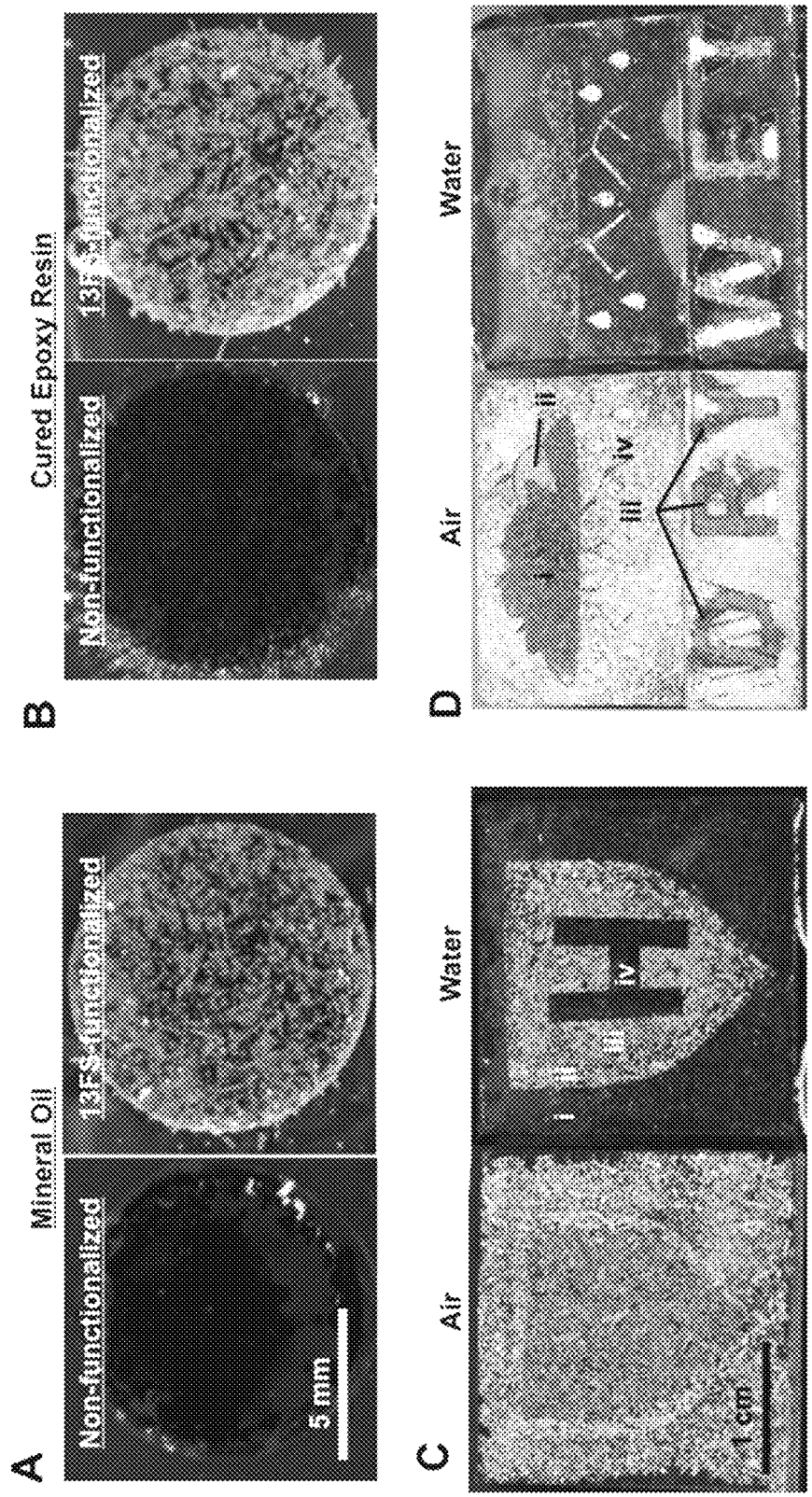
FIGS. 17A-17D shows optical images of photonic crystal particles that repel certain liquids patterned near the center and photonic crystal particles that attract the liquid near the outside of the substrate in accordance with certain embodiments.

For example, FIGS. 17A and 17B shows two sets of photographs (diffuse illumination) comparing non-functionalized photonic bricks (left in each set) with those functionalized with 1H,1H,2H,2H-tridecafluorooctyl trichlorosilane (13FS) (right in each set) when immersed in mineral oil (FIG. 17A) and UV-curable epoxy resin (FIG. 17B, UVO-114, imaged following UV-curing). All four samples are freeform photonic bricks with the lattice spacing being 350 nm and containing 0.7% of gold nanoparticles (by matrix volume). This functionalization allows the air porosity to be maintained in liquid formulations. FIGS. 17C and 17D show adaptive paints. Photographs (diffuse illumination) of freeform photonic bricks (all with lattice spacing=350 nm) painted onto a surface with patterns of color and patterned surface chemistry, revealing different images when wet and dry. FIG. 17C shows a pattern of color: i,ii—Freeform photonic bricks with no plasmonic absorber, iii, iv—freeform with 0.7% gold nanoparticles content (by matrix volume); Pattern of surface functionalization: i,iv—not functionalized, ii,iii—13FS-functionalized. When immersed in water, brightness of color dramatically diminishes in only the non-functionalized regions where the air pores have become filled. FIG. 17D shows a more complex color pattern produced by varying AuNP content (i—1.3%, ii—0.4%, iii—0.7%, iv—0%) showing the same region-selective color change in water. Color is retained in regions that were selectively functionalized with 13FS (all of region i, and the portions of regions iii and iv that remain bright in water). Other silanes, such as 1H,1H,2H,2H-Perfluorodecyltriethoxysilane, 1H,1H,2H,2H-Perfluorooctyltriethoxysilane, 11-(3,3,4,4,5,5,6,6,7,7,8,8,8-tridecafluoro-1-octyloxy)-undec-1-yl trimethoxysilane, 11-(pentafluorobenzyloxy)-undec-1-yl trimethoxysilane, Dimethoxy-methyl(3,3,3-trifluoropropyl)silane, 1H,1H,2H,2H-Perfluorododecyltrichlorosilane Trichloro(3,3,3-trifluoropropyl)silane_and generally perfluorinated-alkyl alkoxy silanes, pefluorinated-alkyl chlorosilanes, pefluorinated-alkyl chloro methyl silanes and other silanes possessing fluorinated functional moieties and and other silanes that hinder the penetration of a desired liquid into the pores can be utilized. Generally, any surface functionality that forms an intrinsic contact angle with the given liquid that is larger than the angle of the solid matrix at the opening between two pores can be chosen. Such surface functionalization can help reduce a liquid from infiltrating the pores and thus reduce the color appearance by lowering the refractive index contrast.

Figure 18:
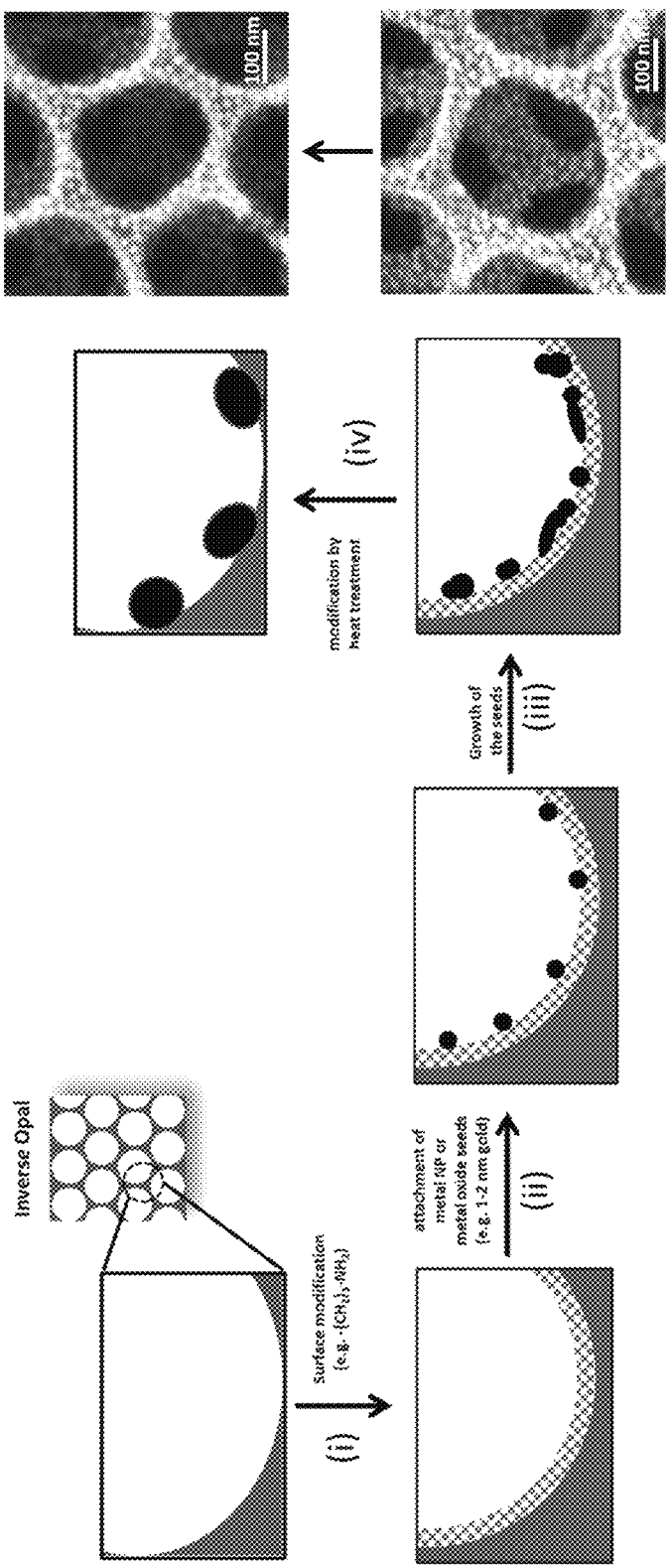
FIG. 18 shows a schematic illustration post-modification of photonic crystal with selective absorbers in accordance with certain embodiments.

In alternative embodiments, as shown in FIG. 18, chemical modification of the photonic structure with a monolayer having anchoring function for nanoparticle attachment can be carried out as shown in (i). For example, the surfaces of the photonic structure can be modified with —(CH$_2$)$_3$—NH$_2$ groups that can be utilized to attach metal (e.g., 1-2 nm gold) nanoparticles or other metal oxide seeds. Then, small (seeds) nanoparticles can be immobilized on the surface of the photonic crystal solid matrix as shown in (ii). The small nanoparticles can be additionally grown by supplying more metal precursor and reducing agent as shown in (iii). The resultant composite photonic crystal structure can be heat treated to produce a photonic crystal with strong coloration due to the formation of well-defined bigger nanoparticles at the air/solid interface as shown in (iv). The method can be applied to other photonic crystal systems and utilize additional metals. Additional surface functionalization groups include but are not limited to silane moieties, phosphoric acid compounds, positively charged functional groups, negatively charged functional groups, thiols, carboxylic acids and others.

In yet other alternative embodiments, the photonic crystal particles can be functionalized to prevent or substantially reduce infiltration of other components of a cosmetic or paint formulation into the pores of the photonic crystal. Hence, diminished brilliance or loss of structural color can be prevented or delayed.

Advantages

There are numerous advantages to the present disclosure over conventional systems.

First, achieving a highly saturated, bright red color in coatings has been heretofore only achieved using organic pigments approved for only a narrow spectrum of applications (i.e. car coatings). Their potential toxicity limits their use in corporal applications. Strategies have been devised to overcome these regulatory challenges, including the use of tunable structural color. The controlled inclusion of spectrally selective absorbing components into photonic crystal particles can create structurally colored materials that can be used in a broad range of applications (e.g., cosmetics, paints for interior/living spaces, biomedical materials, sign paints, paints in automotive, consumer applications and the like). The ability to optimize the optical properties as desired through varying specifications, such as selection of material, selection of photonic crystal structure, selection of photonic crystal materials, selection of spectrally selective absorbing components, and the like removes the need to rely on organic dyes for obtaining color. As such, the resultant structural color can be both non-toxic and permanently resistant to bleaching damage. The matrix can further have additional properties such as antimicrobial or anti-inflammatory properties, UV absorption, photocatalysis, absorption of odors or contaminants, release of active molecules (drugs, odors), and others.

Second, the present disclosure utilizes spectrally selective absorbing components rather than an absorbing component that indiscriminately absorb all wavelengths of light, including resonant wavelengths of the photonic crystals. It should be noted that use of absorbing components that indiscriminately absorb even the resonant wavelengths of the photonic crystals can provide some color and contrast enhancement. However, such systems provide colors that can be less intense due to undesired absorption at the constructive interference wavelength of the structural color as compared to systems with spectrally-selective absorbers, presented herein, with an absorption band that specifically complements the photonic crystals resonance.

Figures 19A, 19B:
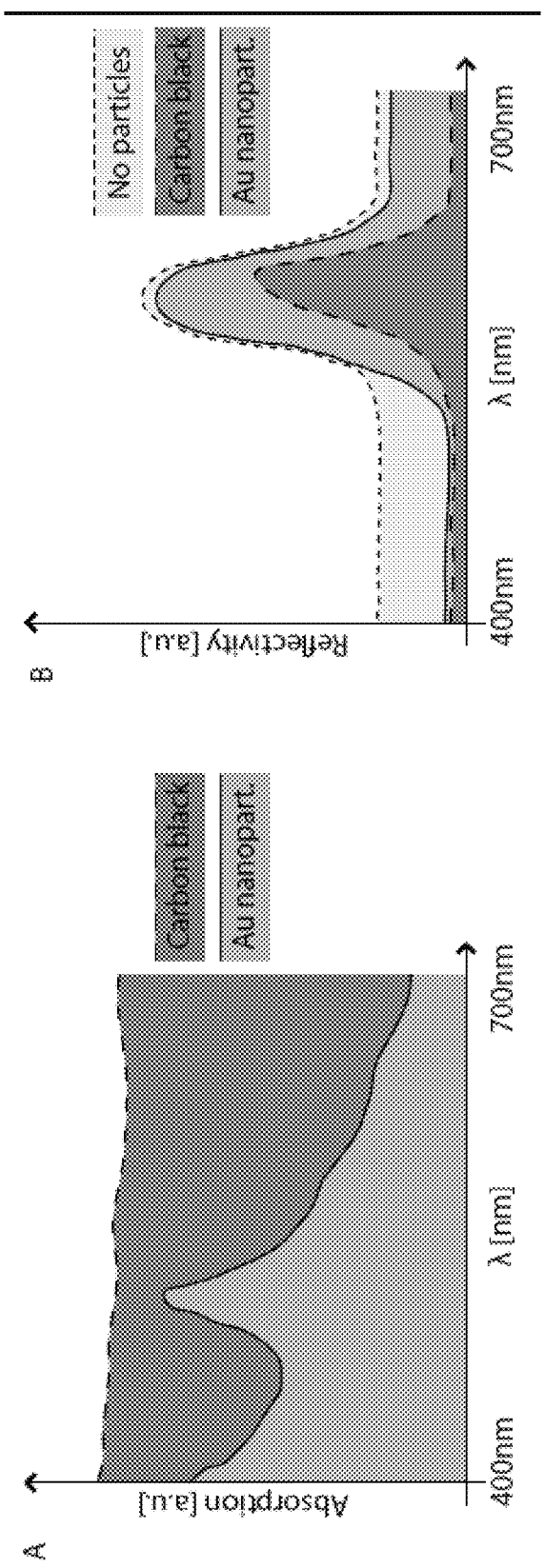
FIGS. 19A-19B show absorption spectra of different spectral absorbing components and reflectance spectra of the different spectral absorbing components embedded within a photonic crystal in accordance with certain embodiments.

FIGS. 19A and 19B schematically illustrate this effect using gold nanoparticles ("AuNPs") as an exemplary spectrally selective absorbing components and carbon black as an exemplary indiscriminately absorbing component (see FIG. 19A). As shown in FIG. 19B, when no absorbing components are utilized (i.e., only photonic crystal particle), a predominant reflectivity centered around the resonant wavelength of the photonic crystal can occur. However, this is accompanied by the undesired side-effect that other wavelengths can also be reflected by unspecific scattering as well, which can in some instances even cause the material to appear white.

Figures 19C, 19D, 19E:
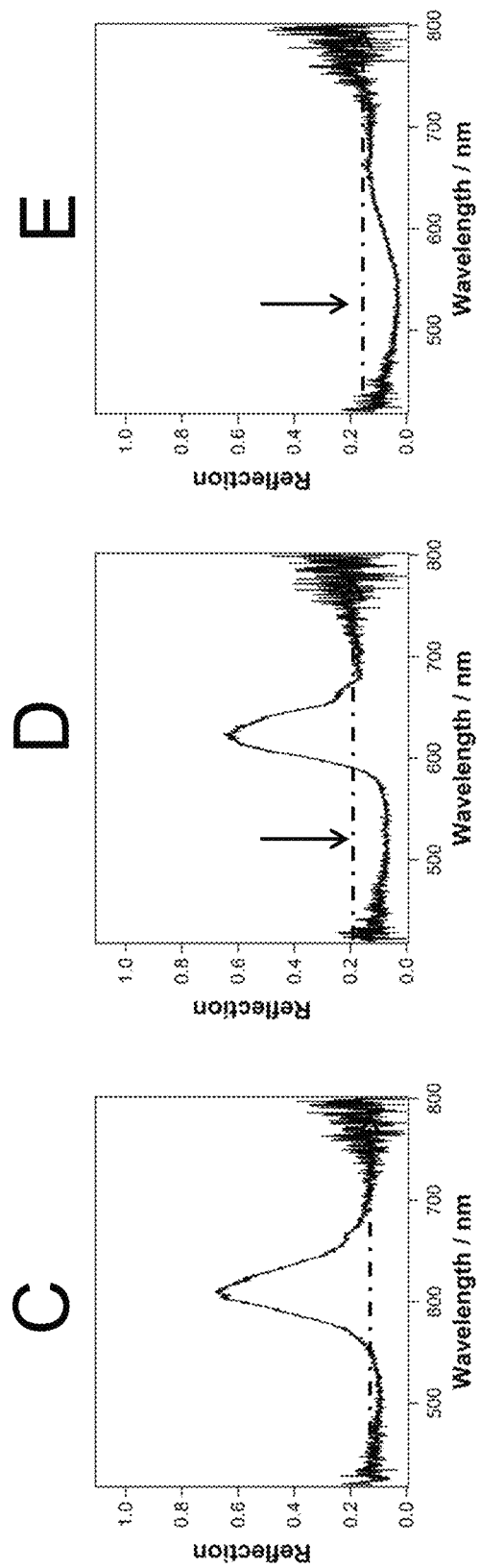
FIGS. 19C-19E shows reflectance spectra of gold nanoparticles within a photonic crystal ball, photonic crystal ball without any gold nanoparticles, and gold nanoparticles within a non-photonic crystal ball, in accordance with certain embodiments.

FIG. 19C shows a reflectance spectrum of a photonic crystal ball without any gold nanoparticles that serve as spectrally selective absorbing components. As shown, a resonant wavelength near 610 nm is observed. FIG. 19D shows a reflectance spectrum of a photonic crystal ball containing gold nanoparticles. As shown, the gold nanoparticles decrease reflection near 520 nm (blue/green) while the resonant wavelength peak near 610 nm is still observed. FIG. 19E shows a reflectance spectrum of gold nanoparticles inside a disordered array of a ball. As shown, the resonant wavelength at 610 disappears and only a suppressed reflectance near 520 nm (blue/green) due to the gold nanoparticles can be observed.

By adding spectrally selective absorbing component (e.g., gold nanoparticles), which suppresses most other visible wavelengths except for those wavelengths near the resonant wavelength of the photonic crystal structure, suppression of other wavelengths can be obtained without losing reflectance for the resonant wavelengths. This is particularly true for dispersible particles such as these, which have incomplete photonic bandgaps and lots of scattering.

Figures 20A, 20B:
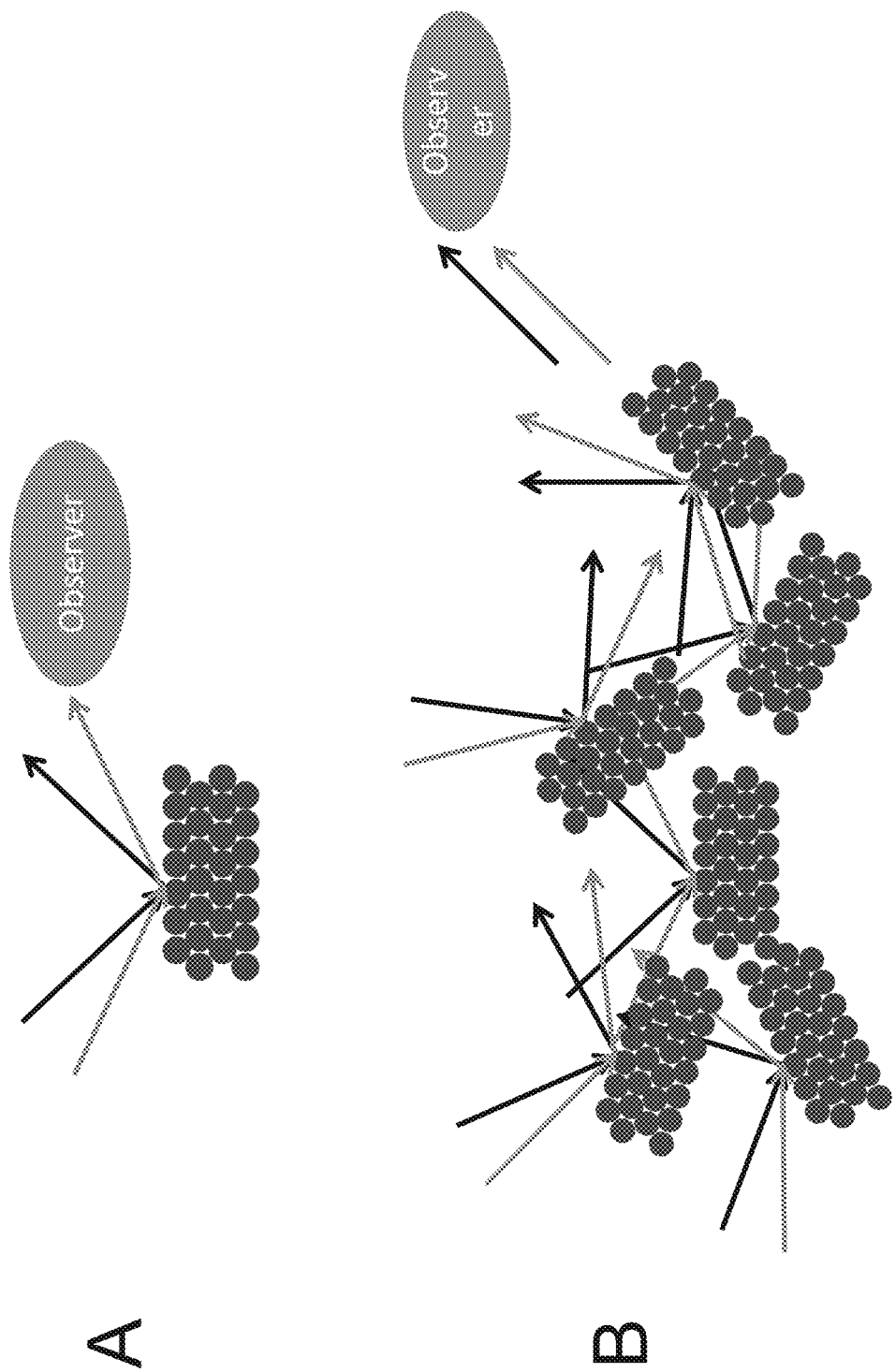
FIGS. 20A and 20B show schematic illustrations of how light can reflects off different photonic crystal particles in accordance with certain embodiments.

FIG. 20 shows how an aggregate of photonic crystal particles with the spectrally selective absorbing components can provide a desired structural color. As shown in FIG. 20A, if a thin film of photonic crystal is provided having one orientation, an observer observes a particular constructive interference wavelengths depending on the viewing angle. However, as shown in FIG. 20B, when photonic crystal particles are randomly oriented with respect to one another, each particle will have a different orientation compared to neighbors and an observer will observe an average over all of these constructive interference wavelengths. This reduces the angular dependence of the observed structural color. However, without any absorbing components, scattering of light at boundaries, edges and imperfections of the individual particles may lead to an overall whitish appearance. The introduction of a spectrally absorbing agent will lead to a reduction of scattered light in undesired parts of the visible spectrum. For example, when adding gold nanoparticles, their absorption in the blue/green part of the spectrum removes these colors from the scattered light and thus gives a more reddish overall appearance.

The present disclosure provides photonic crystal particles that have spectrally selective absorbing components that are selected so that the absorption near the resonant wavelengths of the photonic crystal is reduced.

Third, the present disclosure provides control over additional optical effects (so-called complex color effects), such as sparkle effects, iridescence, angular independence and the like. For example, when sufficiently large and/or anisotropic photonic crystal particles are utilized, each individual photonic particle or large grains of particles all arranged in nearly the same manner can provide localized iridescent or sparkle effects (see FIG. 21A, FIG. 12D-E). When the photonic crystal particles are deposited in the form of a film, each of the little reflectors has different orientation and hence for a couple of photonic crystal particles will always have a specular reflection condition for part of the room's illumination pattern. Changing the position in the room, this becomes true for other photonic crystal particles on the sample in different orientations. As a result, a highly vivid color appears somewhat similar to the always-changing specular reflection on a rippled water surface. This is usually a very prominent effect because human eyes are trained towards fast varying reflexes of intensity.

Fourth, the present disclosure contemplates a photonic crystal particle having a predetermined minimum number of repeat units. As disclosed herein, the predetermined minimum number of repeat units is related to the desired reflected resonant wavelength of the photonic crystal, the full-width at half maximum of the reflectance peak, and the refractive index constrast of the photonic crystal. Photonic crystal particles having at least the predetermined number of minimum repeat units provide a sufficiently strong resonant effects of a photonic crystal despite the presence of the absorbers that can not only absorb light but also provide defects in the photonic crystal structure. Such optimized photonic crystal particle size provides the further improvements to the structural color that is observed when utilizing photonic crystal particles as the intensity of the observed reflected color can be further improved.

Fifth, the fabrication techniques with sacrificial patterned substrates described herein allow fabrication of any desired photonic crystal particle size with high yield. In certain embodiments, even yields up to 100% of the photonic crystal particles within each and every channel can be realized. The use of a sacrificial bottom layer as well as the channel walls or using emulsion technique provide improved fabrication techniques over conventional art. The fabrication technique further provides the ability to control the shape of the photonic crystal particles, which can be used to provide further desired spectral properties.

Figure 21:
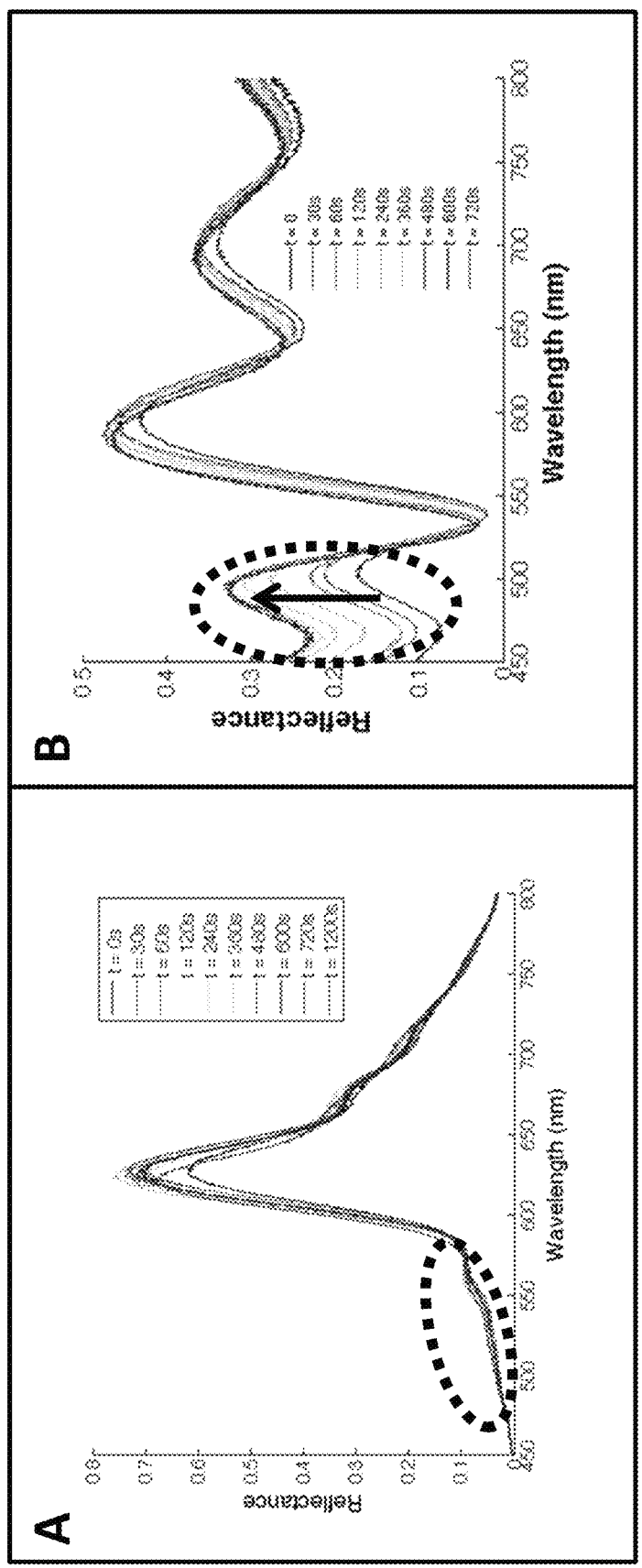
FIG. 21 demonstrates improved photostability of the present disclosure in accordance with certain embodiments.

Sixth, the photonic crystal particles described herein provide improved photostability. FIG. 21 shows comparison of photostability (under UV irradiation 130 mW/cm$^2$ at 365 nm) of inverse-opal photonic crystals doped with different types of spectrally selective absorbers. FIG. 21A shows the reflectance spectra of gold nanoparticle-containing photonic crystal particles demonstrating good photostability when short wavelengths are absorbed by AuNPs. FIG. 21B shows the reflectance spectra of an organic dye (poly-Disperse-Red-1-co-acrylic-acid) in a photonic crystal particle used to suppress the shorter wavelengths, which increases in intensity over time due to photobleaching.

Seventh, the photonic crystal particles can be provided with any number of binding reagents that can provide selective absorption of any particular analytes. Upon absorption of such analytes, the structural color may disappear or become altered due to the change in the refractive index contrast in the photonic crystal that can be useful in a wide range of applications, such as sensor, markers, and the like.

Applications

Numerous different applications can be envisioned. Commercial interests in tunable color, "smart" paint or cosmetic product could be satisfied by photonic crystal-based structural color pigments. Further, the ability to easily scale-up production of such photonic crystal particles having spectrally selective absorbing components for dispersion into a paint greatly increases its flexibility in final implementation, such as power-free road signs, beverage quality control, package authentication, tamper-indication, smart paints, and even entertainment, novelty consumer products, and various cosmetic applications.

Particularly, in cosmetic applications, toxic chemicals, such as those found in certain organic dyes, cannot be utilized. However, by utilizing the structurally colored materials described herein, which are based on medically approved materials, such as gold, silver, silica, titania, and the like, these materials can be used in cosmetic applications. Moreover, by selection of the materials, additional beneficial properties for cosmetic applications, such as UV absorption, antimicrobial properties, controlled release of particular drugs, controlled absorption of undesirable moieties (e.g., oils from skin), and the like can be provided. In addition, the materials described herein provide improved resistance to photobleaching, allowing use for longer periods.

Upon review of the description and embodiments provided herein, those skilled in the art will understand that modifications and equivalent substitutions may be performed in carrying out the invention without departing from the essence of the invention. Thus, the invention is not meant to be limiting by the embodiments described explicitly above.

What is claimed is:

1. A pigment comprising:
a plurality of photonic crystal particles dispersed in a medium, each photonic crystal particle containing a plurality of spectrally selective absorbing components dispersed within each photonic crystal particle that suppress wavelengths outside of a resonant wavelength of each photonic crystal particle and selectively absorb electromagnetic radiation without substantially absorbing electromagnetic radiation near the resonant wavelength of each photonic crystal particle, wherein
the spectrally selective absorbing components comprise spherical gold nanoparticles with a size from 5 nm-80 nm, which do not significantly absorb at 650 nm but selectively absorb other visible wavelengths for producing a red color,
the spectrally selective absorbing components comprise gold rods having a short axis diameter of 10 nm, a long axis length of 50-60 nm and an aspect ratio of 5-6, and have an absorbing wavelength that is centered around 520 nm and 1000 nm with an absorption minimum centered around about 620 nm for producing an orange-red to brown color,
the spectrally selective absorbing components comprise gold hollow spheres having a core diameter of 600 nm and a shell of 7 nm and have an absorbing wavelength centered at around 910 nm with an absorption minimum below 650 nm for producing a green color,
the spectrally selective absorbing components comprise silver nanoplates having a diameter of 40-50 nm and a thickness of 10 nm and have an absorbing wavelength centered at around 550 nm with an absorption minimum centered around 450 nm and above 700 nm for producing a purple/red color,
the spectrally selective absorbing components comprise silver nanoplates having a diameter of 60-80 nm and a thickness of 10 nm and have an absorbing wavelength centered at around 650 nm with an absorption minimum below 480 nm for producing a blue color, or
the spectrally selective absorbing components comprise silver nanoplates having a diameter of 110-150 nm and a thickness of 10 nm and have an absorbing wavelength centered at around 950 nm with an absorption minimum centered around 520 nm for producing a green color,
wherein each photonic crystal particle has a predetermined minimum number of repeat units of a photonic crystal structure, wherein the predetermined minimum number of repeat units is related to the resonant wavelength, the full-width at half maximum of the resonant wavelength, and the refractive index contrast in the photonic crystal.

2. The pigment of claim 1, wherein the photonic crystal structure is an inverse or a direct opal structure.

3. The pigment of claim 1, wherein the pigment exhibits a red structural color.

4. The pigment of claim 1, wherein the photonic crystal particles are bricks or spheres.

5. The pigment of claim 1, wherein the photonic crystal structure is an inverse opal structure and the spectrally selective absorbing components are gold nanoparticles and the pigment exhibits a red structural color.

6. The pigment of claim 1, wherein said photonic crystal particles comprise silica, titania, zirconia, alumina, polymeric materials, silicone, carbonates, sulfates, phosphates, inorganic salts, quartz, sapphire, silicon, and combinations thereof.

7. The pigment of claim 1, wherein the photonic crystals particles have a coating that provides UV protection properties, antimicrobial properties, anti-inflammatory properties, controlled release of desired molecules, photocatalytic properties or combinations thereof.

8. The pigment of claim 1, wherein the plurality of particles provide an angular independent structural color to an observer regardless of angles of observation.

9. The pigment of claim 1, wherein the pigment is used in paints, cosmetics, pastes or combinations thereof.

10. The pigment of claim 1, wherein the predetermined minimum number of repeat units of the photonic crystal structure is 12 repeat units.

11. A method for forming the pigment of claim 1, the method comprising:
forming a sacrificial layer over a substrate; forming one or more channel walls over said sacrificial layer; forming the plurality of photonic crystal particles within said one or more channel walls, wherein said plurality of photonic crystal particles comprise the spectrally selective absorbing component that suppresses wavelengths outside of the resonant wavelength of the photonic crystal particle and selectively absorbs electromagnetic radiation without substantially absorbing electromagnetic radiation near the resonant wavelength of the photonic crystal particle, and wherein each photonic crystal particle has at least the predetermined minimum number of repeat units of the photonic crystal structure, wherein the predetermined minimum number of repeat units is related to the resonant wavelength, the full-width at half maximum of the resonant wavelength, and the refractive index contrast in the photonic crystal;
dispersing the plurality of photonic crystal particles into the medium, wherein the spectrally selective absorbing components comprise spherical gold nanoparticles with a size from 5 nm-80 nm, which do not significantly absorb at 650 nm but selectively absorb other visible wavelengths for producing a red color,
the spectrally selective absorbing components comprise gold rods having a short axis diameter of 10 nm, a long axis length of 50-60 nm and an aspect ratio of 5-6, and have an absorbing wavelength that is centered around 520 nm and 1000 nm with an absorption minimum centered around about 620 nm for producing an orange-red to brown color,
the spectrally selective absorbing components comprise gold hollow spheres having a core diameter of 600 nm and a shell of 7 nm and have an absorbing wavelength centered at around 910 nm with an absorption minimum below 650 nm for producing a green color, the spectrally selective absorbing components comprise silver nanoplates having a diameter of 40-50 nm and a thickness of 10 nm and have an absorbing wavelength centered at around 550 nm with an absorption minimum centered around 450 nm and above 700 nm for producing a purple/red color,
the spectrally selective absorbing components comprise silver nanoplates having a diameter of 60-80 nm and a thickness of 10 nm and have an absorbing wavelength centered at around 650 nm with an absorption minimum below 480 nm for producing a blue color, or the spectrally selective absorbing components comprise silver nanoplates having a diameter of 110-150 nm and a thickness of 10 nm and have an absorbing wavelength centered at around 950 nm with an absorption minimum centered around 520 nm for producing a green color.

12. The method of claim 11, wherein said sacrificial layer and said one or more channel walls are formed using a photoresist.

13. The method of claim 11, wherein said forming the photonic crystal structure comprises providing one or more colloidal particles within said one or more channel walls.

14. The method of claim 13, wherein said forming the photonic crystal structure further comprises providing a matrix material surrounding said one or more colloidal particles and removing said one or more colloidal particles.

15. The method of claim 11, wherein said removing comprises dissolution or heating of said sacrificial layer and said on or more channel walls.

16. The method of claim 11, wherein the predetermined minimum number of repeat units is 12.

17. A method for forming the pigment of claim 1, the method comprising:
forming an aqueous mixture of colloidal particles and spectrally selective absorbing components;
mixing said aqueous mixture with an oil to form emulsion droplets, each droplet comprising water, colloidal particles and spectrally selective absorbing components; and removing said water from said emulsion droplets to form the plurality of photonic crystal particles, and
dispersing the plurality of photonic crystal particles into the medium, wherein said plurality of photonic crystal particles comprise the spectrally selective absorbing component that suppresses wavelengths outside of the resonant wavelength of the photonic crystal particle and selectively absorbs electromagnetic radiation without substantially absorbing electromagnetic radiation near the resonant wavelength of the photonic crystal particle and wherein each photonic crystal particle has the predetermined minimum number of repeat units of the photonic crystal structure, wherein the predetermined minimum number of repeat units is related to the resonant wavelength, the full-width at half maximum of the resonant wavelength, and the refractive index contrast in the photonic crystal, wherein the spectrally selective absorbing components comprise spherical gold nanoparticles with a size from 5 nm- 80 nm, which do not significantly absorb at 650 nm but selectively absorb other visible wavelengths for producing a red color,
the spectrally selective absorbing components comprise gold rods having a short axis diameter of 10 nm, a long axis length of 50-60 nm and an aspect ratio of 5-6, and have an absorbing wavelength that is centered around 520 nm and 1000 nm with an absorption minimum centered around about 620 nm for producing an orange-red to brown color,
the spectrally selective absorbing components comprise gold hollow spheres having a core diameter of 600 nm and a shell of 7 nm and have an absorbing wavelength centered at around 910 nm with an absorption minimum below 650 nm for producing a green color, the spectrally selective absorbing components comprise silver nanoplates having a diameter of 40-50 nm and a thickness of 10 nm and have an absorbing wavelength centered at around 550 nm with an absorption minimum centered around 450 nm and above 700 nm for producing a purple/red color,
the spectrally selective absorbing components comprise silver nanoplates having a diameter of 60-80 nm and a thickness of 10 nm and have an absorbing wavelength centered at around 650 nm with an absorption minimum below 480 nm for producing a blue color, or the spectrally selective absorbing components comprise silver nanoplates having a diameter of 110-150 nm and a thickness of 10 nm and have an absorbing wavelength centered at around 950 nm with an absorption minimum centered around 520 nm for producing a green color.

18. The method of claim 17, wherein said aqueous mixture further comprises a matrix material.

19. The method of claim 17, further comprising:
removing said colloidal particles.

20. The method of claim 17, wherein each photonic crystal particles comprise an inverse opal structure and said spectrally selective absorbing components comprise gold nanoparticles or silver nanoparticles.

21. The method of claim 17, wherein said photonic crystal particles comprise silica, titania, zirconia, alumina, polymeric materials, silicone, carbonates, sulfates, phosphates, inorganic salts, quartz, sapphire, silicon, and combinations thereof.

22. The method of claim 17, wherein the predetermined minimum number of repeat units is 12.

* * * * *